(12) United States Patent
Nezu et al.

(10) Patent No.: US 6,759,514 B1
(45) Date of Patent: Jul. 6, 2004

(54) TRANSPORTER POLYPEPTIDE AND METHOD OF PRODUCING SAME

(75) Inventors: Jun-ichi Nezu, Niihari-mura (JP); Asuka Oku, Niihari-mura (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/521,195

(22) Filed: Mar. 7, 2000

Related U.S. Application Data

(63) Continuation-in-part of application No. PCT/JP98/04009, filed on Sep. 7, 1998.

(30) Foreign Application Priority Data

Sep. 8, 1997 (JP) .............................................. 9-260972
May 20, 1998 (JP) ............................................ 10-156660

(51) Int. Cl.[7] ...................... C07K 14/705; C12N 15/12; C12N 15/63; C12N 5/10
(52) U.S. Cl. ..................... 530/350; 435/69.1; 435/71.2; 435/471; 435/252.3; 435/320.1; 435/325
(58) Field of Search ........................ 530/350; 435/69.1, 435/71.1, 71.2, 471, 252.3, 254.11, 320.1, 325

(56) References Cited

U.S. PATENT DOCUMENTS 6,063,623 A  *  5/2000  Koepsell et al. ............. 435/371

FOREIGN PATENT DOCUMENTS

| EP | 0 699 753 A | 3/1996 |
| JP | 8-81497 A | 3/1996 |
| WO | WO 97/42321 A1 | 11/1997 |
| WO | WO 00/14210 A1 | 3/2000 |

OTHER PUBLICATIONS

Mikayama et al. Proc. Natl. Acad. Sci. USA vol. 90 pp. 10056–10060, 1993.*
Vaet et al, Biochemistry. John Wiley & Sons, Inc. pp. 126–128 and 228–234, 1990.*
Gorboulev et al., "Cloning and characterization of two human polyspecific . . . ", 1997, *DNA and Cell Biology*, vol. 16(7);871–881.
Schweifer et al., "The L–chi–1 gene maps to mouse . . . ", 1996, *Mammalian Genome*, vol. 7(10);735–740.
Chun et al., "Expression of human polyspecific renal organic . . . ", 1997, *J. Pharmaceutical Sciences*, vol. 86(6);753–755.
Lopez–nieto et al., "Molecular cloning and characterization of NKT . . . ", 1997, *J. Biolog. Chem.*, vol. 272(10);6471–6478.
GenBank Accession No. AA428395, May 25, 1997.
GenBank Accession No. AA024584, Aug. 14, 1996.
GenBank Accession No. AA189399, Jan. 20, 1997.
Simonson et al., "Molecular cloning and characterization of a novel . . . ", 1994, *J. Cell Science*, vol. 107(4);1065–1072.
Gruendemann et al., "Primary structure and functional expression of the apical organic . . . ", 1997, *J. Biol. Chem.*, vol. 272(16);10408–10413.
Zhang et al., "Cloning and functional expression of a human liver . . . ", 1997, *Molecular Pharmacology*, vol. 51(6);913–921.
European Search Report for Application No. 98941751.4–2403–JP9804009, mailed Sep. 16, 2002.
English Translation of WO 00/14210 A1.
Grundemann D. et al., "Drug excretion mediated by a new prototype . . . ", Nature, 1994, 372(6506);549–52.
Okuda M. et al., "cDNA Cloning and Functional Expression of a Novel Rat . . . ", Biochem Biophys Res Commun, 1996, 224(2);500–7.
Wang et al., "Mutations in the . . . ," Proc. Natl. Acad. Sci. USA, 96:2356–2360, 1999.
Wu et al., "cDNA Sequence . . . ," Biochemical and Biophysical Research Communications, 246:589–595, 1998.
Yabuuchi et al., "Novel Membrane . . . ," The Journal of Pharmacology and Experimental Therapeutics, 289(2):768–773, 1999.
Tamai et al., "Molecular and Functional . . . ," The Journal of Biological Chemistry, 273(32):20378–20382, 1998.
Nezu et al., "Primary systemic . . . ," Nature Genetics, 21:91–94, 1999.
Tamai et al., "Cloning and characterization . . . ," FEBS Letter, 419:107–111, 1997.

* cited by examiner

*Primary Examiner*—Prema Mertz
(74) *Attorney, Agent, or Firm*—Fish & Richardson PC

(57) ABSTRACT

Novel genes significantly homologous to organic cation transporters OCT1 and OCT2 have been successfully isolated by screening a fetal gene library by random sequencing. Proteins encoded by these genes function as transporters of various organic cations.

28 Claims, 13 Drawing Sheets

FIG. 3

SEQUENCE LISTING

<160> NUMBER OF SEQ ID NOS: 33

<210> SEQ ID NO 1
<211> LENGTH: 551
<212> TYPE: PRT
<213> ORGANISM: Homo sapiens

<400> SEQUENCE: 1

```
Met Arg Asp Tyr Asp Glu Val Ile Ala Phe Leu Gly Glu Trp Gly Pro
 1               5                  10                  15

Phe Gln Arg Leu Ile Phe Phe Leu Leu Ser Ala Ser Ile Ile Pro Asn
            20                  25                  30

Gly Phe Asn Gly Met Ser Val Val Phe Leu Ala Gly Thr Pro Glu His
        35                  40                  45

Arg Cys Arg Val Pro Asp Ala Ala Asn Leu Ser Ser Ala Trp Arg Asn
    50                  55                  60

Asn Ser Val Pro Leu Arg Leu Arg Asp Gly Arg Glu Val Pro His Ser
65                  70                  75                  80

Cys Ser Arg Tyr Arg Leu Ala Thr Ile Ala Asn Phe Ser Ala Leu Gly
                85                  90                  95

Leu Glu Pro Gly Arg Asp Val Asp Leu Gly Gln Leu Glu Gln Glu Ser
            100                 105                 110

Cys Leu Asp Gly Trp Glu Phe Ser Gln Asp Val Tyr Leu Ser Thr Val
        115                 120                 125

Val Thr Glu Trp Asn Leu Val Cys Glu Asp Asn Trp Lys Val Pro Leu
130                 135                 140

Thr Thr Ser Leu Phe Phe Val Gly Val Leu Leu Gly Ser Phe Val Ser
145                 150                 155                 160

Gly Gln Leu Ser Asp Arg Phe Gly Arg Lys Asn Val Leu Phe Ala Thr
                165                 170                 175

Met Ala Val Gln Thr Gly Phe Ser Phe Leu Gln Ile Phe Ser Ile Ser
            180                 185                 190

Trp Glu Met Phe Thr Val Leu Phe Val Ile Val Gly Met Gly Gln Ile
        195                 200                 205

Ser Asn Tyr Val Val Ala Phe Ile Leu Gly Thr Glu Ile Leu Gly Lys
    210                 215                 220

Ser Val Arg Ile Ile Phe Ser Thr Leu Gly Val Cys Thr Phe Phe Ala
225                 230                 235                 240

Val Gly Tyr Met Leu Leu Pro Leu Phe Ala Tyr Phe Ile Arg Asp Trp
                245                 250                 255

Arg Met Leu Leu Leu Ala Leu Thr Val Pro Gly Val Leu Cys Val Pro
            260                 265                 270

Leu Trp Trp Phe Ile Pro Glu Ser Pro Arg Trp Leu Ile Ser Gln Arg
        275                 280                 285

Arg Phe Arg Glu Ala Glu Asp Ile Ile Gln Lys Ala Ala Lys Met Asn
    290                 295                 300

Asn Thr Ala Val Pro Ala Val Ile Phe Asp Ser Val Glu Glu Leu Asn
305                 310                 315                 320

Pro Leu Lys Gln Gln Lys Ala Phe Ile Leu Asp Leu Phe Arg Thr Arg
                325                 330                 335

Asn Ile Ala Ile Met Thr Ile Met Ser Leu Leu Leu Trp Met Leu Thr
            340                 345                 350

Ser Val Gly Tyr Phe Ala Leu Ser Leu Asp Ala Pro Asn Leu His Gly
```

-continued

```
                    355                 360                 365
Asp Ala Tyr Leu Asn Cys Phe Leu Ser Ala Leu Ile Glu Ile Pro Ala
        370                 375                 380

Tyr Ile Thr Ala Trp Leu Leu Arg Thr Leu Pro Arg Arg Tyr Ile
385                 390                 395                 400

Ile Ala Ala Val Leu Phe Trp Gly Gly Val Leu Leu Phe Ile Gln
                405                 410                 415

Leu Val Pro Val Asp Tyr Tyr Phe Leu Ser Ile Gly Leu Val Met Leu
                420                 425                 430

Gly Lys Phe Gly Ile Thr Ser Ala Phe Ser Met Leu Tyr Val Phe Thr
        435                 440                 445

Ala Glu Leu Tyr Pro Thr Leu Val Arg Asn Met Ala Val Gly Val Thr
    450                 455                 460

Ser Thr Ala Ser Arg Val Gly Ser Ile Ile Ala Pro Tyr Phe Val Tyr
465                 470                 475                 480

Leu Gly Ala Tyr Asn Arg Met Leu Pro Tyr Ile Val Met Gly Ser Leu
                485                 490                 495

Thr Val Leu Ile Gly Ile Phe Thr Leu Phe Phe Pro Glu Ser Leu Gly
                500                 505                 510

Met Thr Leu Pro Glu Thr Leu Glu Gln Met Gln Lys Val Lys Trp Phe
            515                 520                 525

Arg Ser Gly Lys Lys Thr Arg Asp Ser Met Glu Thr Glu Glu Asn Pro
        530                 535                 540

Lys Val Leu Ile Thr Ala Phe
545                 550

<210> SEQ ID NO 2
<211> LENGTH: 2135
<212> TYPE: DNA
<213> ORGANISM: Homo sapiens
<220> FEATURE:
<221> NAME/KEY: CDS
<222> LOCATION: (147)..(1799)

<400> SEQUENCE: 2
ccccggcttc gcgccccaat ttctaacagc ctgcctgtcc cccgggaacg ttctaacatc      60
cttggggagc gccccagcta caagacactg tcctgagaac gctgtcatca cccgtagttg     120
caagtttcgg agcggcagtg ggaagc atg cgg gac tac gac gag gtg atc gcc     173
                              Met Arg Asp Tyr Asp Glu Val Ile Ala
                                1               5 ttc ctg ggc gag tgg ggg ccc ttc cag cgc ctc atc ttc ttc ctg ctc     221
Phe Leu Gly Glu Trp Gly Pro Phe Gln Arg Leu Ile Phe Phe Leu Leu
 10              15                  20                  25 agc gcc agc atc atc ccc aat ggc ttc aat ggt atg tca gtc gtg ttc     269
Ser Ala Ser Ile Ile Pro Asn Gly Phe Asn Gly Met Ser Val Val Phe
                30                  35                  40 ctg gcg ggg acc ccg gag cac cgc tgt cga gtg ccg gac gcc gcg aac     317
Leu Ala Gly Thr Pro Glu His Arg Cys Arg Val Pro Asp Ala Ala Asn
            45                  50                  55 ctg agc agc gcc tgg cgc aac aac agt gtc ccg ctg cgg ctg cgg gac     365
Leu Ser Ser Ala Trp Arg Asn Asn Ser Val Pro Leu Arg Leu Arg Asp
        60                  65                  70 ggc cgc gag gtg ccc cac agc tgc agc cgc tac cgg ctc gcc acc atc     413
Gly Arg Glu Val Pro His Ser Cys Ser Arg Tyr Arg Leu Ala Thr Ile
    75                  80                  85 gcc aac ttc tcg gcg ctc ggg ctg gag ccg ggc cgc gac gtg gac ctg     461
Ala Asn Phe Ser Ala Leu Gly Leu Glu Pro Gly Arg Asp Val Asp Leu
```

-continued

| | | | | | | | | | | | | |
|---|---|---|---|---|---|---|---|---|---|---|---|---|
| | 90 | | | 95 | | | 100 | | | 105 | | |
| ggg | cag | ctg | gag | cag | gag | agc | tgc | ctg | gat | ggc | tgg | gag | ttc | agc | cag | 509 |
| Gly | Gln | Leu | Glu | Gln | Glu | Ser | Cys | Leu | Asp | Gly | Trp | Glu | Phe | Ser | Gln | |
| | | | 110 | | | | | 115 | | | | 120 | | | | |
| gac | gtc | tac | ctg | tcc | acc | gtc | gtg | acc | gag | tgg | aat | ctg | gtg | tgt | gag | 557 |
| Asp | Val | Tyr | Leu | Ser | Thr | Val | Val | Thr | Glu | Trp | Asn | Leu | Val | Cys | Glu | |
| | | | 125 | | | | | 130 | | | | 135 | | | | |
| gac | aac | tgg | aag | gtg | ccc | ctc | acc | acc | tcc | ctg | ttc | ttc | gta | ggc | gtg | 605 |
| Asp | Asn | Trp | Lys | Val | Pro | Leu | Thr | Thr | Ser | Leu | Phe | Phe | Val | Gly | Val | |
| | | 140 | | | | | 145 | | | | | 150 | | | | |
| ctc | ctc | ggc | tcc | ttc | gtg | tcc | ggg | cag | ctg | tca | gac | agg | ttt | ggc | agg | 653 |
| Leu | Leu | Gly | Ser | Phe | Val | Ser | Gly | Gln | Leu | Ser | Asp | Arg | Phe | Gly | Arg | |
| | 155 | | | | | 160 | | | | | 165 | | | | | |
| aag | aac | gtt | ctc | ttc | gca | acc | atg | gct | gta | cag | act | ggc | ttc | agc | ttc | 701 |
| Lys | Asn | Val | Leu | Phe | Ala | Thr | Met | Ala | Val | Gln | Thr | Gly | Phe | Ser | Phe | |
| 170 | | | | | 175 | | | | | 180 | | | | | 185 | |
| ctg | cag | att | ttc | tcc | atc | agc | tgg | gag | atg | ttc | act | gtg | tta | ttt | gtc | 749 |
| Leu | Gln | Ile | Phe | Ser | Ile | Ser | Trp | Glu | Met | Phe | Thr | Val | Leu | Phe | Val | |
| | | | | 190 | | | | | 195 | | | | | 200 | | |
| atc | gtg | ggc | atg | ggc | cag | atc | tcc | aac | tat | gtg | gta | gcc | ttc | ata | cta | 797 |
| Ile | Val | Gly | Met | Gly | Gln | Ile | Ser | Asn | Tyr | Val | Val | Ala | Phe | Ile | Leu | |
| | | | 205 | | | | | 210 | | | | | 215 | | | |
| gga | aca | gaa | att | ctt | ggc | aag | tca | gtt | cgt | att | ata | ttc | tct | aca | tta | 845 |
| Gly | Thr | Glu | Ile | Leu | Gly | Lys | Ser | Val | Arg | Ile | Ile | Phe | Ser | Thr | Leu | |
| | | 220 | | | | | 225 | | | | | 230 | | | | |
| gga | gtg | tgc | aca | ttt | ttt | gca | gtt | ggc | tat | atg | ctg | ctg | cca | ctg | ttt | 893 |
| Gly | Val | Cys | Thr | Phe | Phe | Ala | Val | Gly | Tyr | Met | Leu | Leu | Pro | Leu | Phe | |
| | 235 | | | | | 240 | | | | | 245 | | | | | |
| gct | tac | ttc | atc | aga | gac | tgg | cgg | atg | ctg | ctg | ctg | gcg | ctg | acg | gtg | 941 |
| Ala | Tyr | Phe | Ile | Arg | Asp | Trp | Arg | Met | Leu | Leu | Leu | Ala | Leu | Thr | Val | |
| 250 | | | | | 255 | | | | | 260 | | | | | 265 | |
| ccg | gga | gtg | ctg | tgt | gtc | ccg | ctg | tgg | tgg | ttc | att | cct | gaa | tct | ccc | 989 |
| Pro | Gly | Val | Leu | Cys | Val | Pro | Leu | Trp | Trp | Phe | Ile | Pro | Glu | Ser | Pro | |
| | | | | 270 | | | | | 275 | | | | | 280 | | |
| cga | tgg | ctg | ata | tcc | cag | aga | aga | ttt | aga | gag | gct | gaa | gat | atc | atc | 1037 |
| Arg | Trp | Leu | Ile | Ser | Gln | Arg | Arg | Phe | Arg | Glu | Ala | Glu | Asp | Ile | Ile | |
| | | | 285 | | | | | 290 | | | | | 295 | | | |
| caa | aaa | gct | gca | aaa | atg | aac | aac | aca | gct | gta | cca | gca | gtg | ata | ttt | 1085 |
| Gln | Lys | Ala | Ala | Lys | Met | Asn | Asn | Thr | Ala | Val | Pro | Ala | Val | Ile | Phe | |
| | | 300 | | | | | 305 | | | | | 310 | | | | |
| gat | tct | gtg | gag | gag | cta | aat | ccc | ctg | aag | cag | cag | aaa | gct | ttc | att | 1133 |
| Asp | Ser | Val | Glu | Glu | Leu | Asn | Pro | Leu | Lys | Gln | Gln | Lys | Ala | Phe | Ile | |
| | 315 | | | | | 320 | | | | | 325 | | | | | |
| ctg | gac | ctg | ttc | agg | act | cgg | aat | att | gcc | ata | atg | acc | att | atg | tct | 1181 |
| Leu | Asp | Leu | Phe | Arg | Thr | Arg | Asn | Ile | Ala | Ile | Met | Thr | Ile | Met | Ser | |
| 330 | | | | | 335 | | | | | 340 | | | | | 345 | |
| ttg | ctg | cta | tgg | atg | ctg | acc | tca | gtg | ggt | tac | ttt | gct | ctg | tct | ctg | 1229 |
| Leu | Leu | Leu | Trp | Met | Leu | Thr | Ser | Val | Gly | Tyr | Phe | Ala | Leu | Ser | Leu | |
| | | | | 350 | | | | | 355 | | | | | 360 | | |
| gat | gct | cct | aat | tta | cat | gga | gat | gcc | tac | ctg | aac | tgt | ttc | ctc | tct | 1277 |
| Asp | Ala | Pro | Asn | Leu | His | Gly | Asp | Ala | Tyr | Leu | Asn | Cys | Phe | Leu | Ser | |
| | | | 365 | | | | | 370 | | | | | 375 | | | |
| gcc | ttg | att | gaa | att | cca | gct | tac | att | aca | gcc | tgg | ctg | cta | ttg | cga | 1325 |
| Ala | Leu | Ile | Glu | Ile | Pro | Ala | Tyr | Ile | Thr | Ala | Trp | Leu | Leu | Leu | Arg | |
| | | 380 | | | | | 385 | | | | | 390 | | | | |
| acg | ctg | ccc | agg | cgt | tat | atc | ata | gct | gca | gta | ctg | ttc | tgg | gga | gga | 1373 |
| Thr | Leu | Pro | Arg | Arg | Tyr | Ile | Ile | Ala | Ala | Val | Leu | Phe | Trp | Gly | Gly | |
| | 395 | | | | | 400 | | | | | 405 | | | | | |
| ggt | gtg | ctt | ctc | ttc | att | caa | ctg | gta | cct | gtg | gat | tat | tac | ttc | tta | 1421 |

```
Gly Val Leu Leu Phe Ile Gln Leu Val Pro Val Asp Tyr Tyr Phe Leu
410                 415                 420                 425 tcc att ggt ctg gtc atg ctg gga aaa ttt ggg atc acc tct gct ttc      1469
Ser Ile Gly Leu Val Met Leu Gly Lys Phe Gly Ile Thr Ser Ala Phe
                430                 435                 440 tcc atg ctg tat gtc ttc act gct gag ctc tac cca acc ctg gtc agg      1517
Ser Met Leu Tyr Val Phe Thr Ala Glu Leu Tyr Pro Thr Leu Val Arg
                445                 450                 455 aac atg gcg gtg ggg gtc aca tcc acg gcc tcc aga gtg ggc agc atc      1565
Asn Met Ala Val Gly Val Thr Ser Thr Ala Ser Arg Val Gly Ser Ile
                460                 465                 470 att gcc ccc tac ttt gtt tac ctc ggt gct tac aac aga atg ctg ccc      1613
Ile Ala Pro Tyr Phe Val Tyr Leu Gly Ala Tyr Asn Arg Met Leu Pro
                475                 480                 485 tac atc gtc atg ggt agt ctg act gtc ctg att gga atc ttc acc ctt      1661
Tyr Ile Val Met Gly Ser Leu Thr Val Leu Ile Gly Ile Phe Thr Leu
490                 495                 500                 505 ttt ttc cct gaa agt ttg gga atg act ctt cca gaa acc tta gag cag      1709
Phe Phe Pro Glu Ser Leu Gly Met Thr Leu Pro Glu Thr Leu Glu Gln
                510                 515                 520 atg cag aaa gtg aaa tgg ttc aga tct ggg aaa aaa aca aga gac tca      1757
Met Gln Lys Val Lys Trp Phe Arg Ser Gly Lys Lys Thr Arg Asp Ser
                525                 530                 535 atg gag aca gaa gaa aat ccc aag gtt cta ata act gca ttc              1799
Met Glu Thr Glu Glu Asn Pro Lys Val Leu Ile Thr Ala Phe
                540                 545                 550 tgaaaaaata tctaccccat ttggtgaagt gaaaaacaga aaaataagac cctgtggaga    1859
aattcgttgt tcccactgaa atggactgac tgtaacgatt gacaccaaaa tgaaccttgc    1919
tatcaagaaa tgctcgtcat acagtaaaact ctggatgatt cttccagata atgtccttgc   1979
tttacaaacc aaccatttct agagagtctc cttactcatt aattcaatga aatggattgg    2039
taagatgtct tgaaaacatg ttagtcaagg actggtaaaa tacatataaa gattaacact    2099
catttccaat catacaaata ctatccaaat aaaaat                              2135
```

<210> SEQ ID NO 3
<211> LENGTH: 557
<212> TYPE: PRT
<213> ORGANISM: Homo sapiens

<400> SEQUENCE: 3

```
Met Arg Asp Tyr Asp Glu Val Thr Ala Phe Leu Gly Glu Trp Gly Pro
 1               5                  10                  15

Phe Gln Arg Leu Ile Phe Phe Leu Leu Ser Ala Ser Ile Ile Pro Asn
                20                  25                  30

Gly Phe Thr Gly Leu Ser Ser Val Phe Leu Ile Ala Thr Pro Glu His
            35                  40                  45

Arg Cys Arg Val Pro Asp Ala Ala Asn Leu Ser Ala Trp Arg Asn
        50                  55                  60

His Thr Val Pro Leu Arg Leu Arg Asp Gly Arg Glu Val Pro His Ser
65                  70                  75                  80

Cys Arg Arg Tyr Arg Leu Ala Thr Ile Ala Asn Phe Ser Ala Leu Gly
                85                  90                  95

Leu Glu Pro Gly Arg Asp Val Asp Leu Gly Gln Leu Glu Gln Glu Ser
                100                 105                 110

Cys Leu Asp Gly Trp Glu Phe Ser Gln Asp Val Tyr Leu Ser Thr Ile
            115                 120                 125
```

-continued

```
Val Thr Glu Trp Asn Leu Val Cys Glu Asp Trp Lys Ala Pro Leu
130                 135                 140
Thr Ile Ser Leu Phe Phe Val Gly Val Leu Leu Gly Ser Phe Ile Ser
145                 150                 155                 160
Gly Gln Leu Ser Asp Arg Phe Gly Arg Lys Asn Val Leu Phe Val Thr
                165                 170                 175
Met Gly Met Gln Thr Gly Phe Ser Phe Leu Gln Ile Phe Ser Lys Asn
            180                 185                 190
Phe Glu Met Phe Val Val Leu Phe Val Leu Val Gly Met Gly Gln Ile
        195                 200                 205
Ser Asn Tyr Val Ala Ala Phe Val Leu Gly Thr Glu Ile Leu Gly Lys
210                 215                 220
Ser Val Arg Ile Ile Phe Ser Thr Leu Gly Val Cys Ile Phe Tyr Ala
225                 230                 235                 240
Phe Gly Tyr Met Val Leu Pro Leu Phe Ala Tyr Phe Ile Arg Asp Trp
                245                 250                 255
Arg Met Leu Leu Val Ala Leu Thr Met Pro Gly Val Leu Cys Val Ala
            260                 265                 270
Leu Trp Trp Phe Ile Pro Glu Ser Pro Arg Trp Leu Ile Ser Gln Gly
        275                 280                 285
Arg Phe Glu Glu Ala Glu Val Ile Ile Arg Lys Ala Ala Lys Ala Asn
290                 295                 300
Gly Ile Val Val Pro Ser Thr Ile Phe Asp Pro Ser Glu Leu Gln Asp
305                 310                 315                 320
Leu Ser Ser Lys Lys Gln Gln Ser His Asn Ile Leu Asp Leu Leu Arg
                325                 330                 335
Thr Trp Asn Ile Arg Met Val Thr Ile Met Ser Ile Met Leu Trp Met
            340                 345                 350
Thr Ile Ser Val Gly Tyr Phe Gly Leu Ser Leu Asp Thr Pro Asn Leu
        355                 360                 365
His Gly Asp Ile Phe Val Asn Cys Phe Leu Ser Ala Met Val Glu Val
370                 375                 380
Pro Ala Tyr Val Leu Ala Trp Leu Leu Leu Gln Tyr Leu Pro Arg Arg
385                 390                 395                 400
Tyr Ser Met Ala Thr Ala Leu Phe Leu Gly Gly Ser Val Leu Leu Phe
                405                 410                 415
Met Gln Leu Val Pro Pro Asp Leu Tyr Tyr Leu Ala Thr Val Leu Val
            420                 425                 430
Met Val Gly Lys Phe Gly Val Thr Ala Ala Phe Ser Met Val Tyr Val
        435                 440                 445
Tyr Thr Ala Glu Leu Tyr Pro Thr Val Val Arg Asn Met Gly Val Gly
450                 455                 460
Val Ser Ser Thr Ala Ser Arg Leu Gly Ser Ile Leu Ser Pro Tyr Phe
465                 470                 475                 480
Val Tyr Leu Gly Ala Tyr Asp Arg Phe Leu Pro Tyr Ile Leu Met Gly
                485                 490                 495
Ser Leu Thr Ile Leu Thr Ala Ile Leu Thr Leu Phe Leu Pro Glu Ser
            500                 505                 510
Phe Gly Thr Pro Leu Pro Asp Thr Ile Asp Gln Met Leu Arg Val Lys
        515                 520                 525
Gly Met Lys His Arg Lys Thr Pro Ser His Thr Arg Met Leu Lys Asp
530                 535                 540
Gly Gln Glu Arg Pro Thr Ile Leu Lys Ser Thr Ala Phe
```

-continued

```
545                550                555

<210> SEQ ID NO 4
<211> LENGTH: 1831
<212> TYPE: DNA
<213> ORGANISM: Homo sapiens
<220> FEATURE:
<221> NAME/KEY: CDS
<222> LOCATION: (124)..(1794)

<400> SEQUENCE: 4
cggacggtct tgggtcgcct gctgcctggc ttgcctggtc ggcggcgggt gccccgcgcg      60
cacgcgcaaa gcccgccgcg ttcccagacc ccaggccgcg ctctgtgggc ctctgagggc     120 ggc atg cgg gac tac gac gag gtg acc gcc ttc ctg ggc gag tgg ggg      168
    Met Arg Asp Tyr Asp Glu Val Thr Ala Phe Leu Gly Glu Trp Gly
    1               5                   10                  15 ccc ttc cag cgc ctc atc ttc ttc ctg ctc agc gcc agc atc atc ccc      216
Pro Phe Gln Arg Leu Ile Phe Phe Leu Leu Ser Ala Ser Ile Ile Pro
                20                  25                  30 aat ggc ttc acc ggc ctg tcc tcc gtg ttc ctg ata gcg acc ccg gag      264
Asn Gly Phe Thr Gly Leu Ser Ser Val Phe Leu Ile Ala Thr Pro Glu
            35                  40                  45 cac cgc tgc cgg gtg ccg gac gcc gcg aac ctg agc agc gcc tgg cgc      312
His Arg Cys Arg Val Pro Asp Ala Ala Asn Leu Ser Ser Ala Trp Arg
        50                  55                  60 aac cac act gtc cca ctg cgg ctg cgg gac ggc cgc gag gtg ccc cac      360
Asn His Thr Val Pro Leu Arg Leu Arg Asp Gly Arg Glu Val Pro His
    65                  70                  75 agc tgc cgc cgc tac cgg ctc gcc acc atc gcc aac ttc tcg gcg ctc      408
Ser Cys Arg Arg Tyr Arg Leu Ala Thr Ile Ala Asn Phe Ser Ala Leu
80                  85                  90                  95 ggg ctg gag ccg ggg cgc gac gtg gac ctg ggg cag ctg gag cag gag      456
Gly Leu Glu Pro Gly Arg Asp Val Asp Leu Gly Gln Leu Glu Gln Glu
                100                 105                 110 agc tgt ctg gat ggc tgg gag ttc agt cag gac gtc tac ctg tcc acc      504
Ser Cys Leu Asp Gly Trp Glu Phe Ser Gln Asp Val Tyr Leu Ser Thr
            115                 120                 125 att gtg acc gag tgg aac ctg gtg tgt gag gac gac tgg aag gcc cca      552
Ile Val Thr Glu Trp Asn Leu Val Cys Glu Asp Asp Trp Lys Ala Pro
        130                 135                 140 ctc aca atc tcc ttg ttc ttc gtg ggt gtg ctg ttg ggc tcc ttc att      600
Leu Thr Ile Ser Leu Phe Phe Val Gly Val Leu Leu Gly Ser Phe Ile
    145                 150                 155 tca ggg cag ctg tca gac agg ttt ggc cgg aag aat gtg ctg ttc gtg      648
Ser Gly Gln Leu Ser Asp Arg Phe Gly Arg Lys Asn Val Leu Phe Val
160                 165                 170                 175 acc atg ggc atg cag aca ggc ttc agc ttc ctg cag atc ttc tcg aag      696
Thr Met Gly Met Gln Thr Gly Phe Ser Phe Leu Gln Ile Phe Ser Lys
                180                 185                 190 aat ttt gag atg ttt gtc gtg ctg ttt gtc ctt gta ggc atg ggc cag      744
Asn Phe Glu Met Phe Val Val Leu Phe Val Leu Val Gly Met Gly Gln
            195                 200                 205 atc tcc aac tat gtg gca gca ttt gtc ctg ggg aca gaa att ctt ggc      792
Ile Ser Asn Tyr Val Ala Ala Phe Val Leu Gly Thr Glu Ile Leu Gly
        210                 215                 220 aag tca gtt cgt ata ata ttc tct acg tta gga gtg tgc ata ttt tat      840
Lys Ser Val Arg Ile Ile Phe Ser Thr Leu Gly Val Cys Ile Phe Tyr
    225                 230                 235 gca ttt ggc tac atg gtg ctg cca ctg ttt gct tac ttc atc cga gac      888
Ala Phe Gly Tyr Met Val Leu Pro Leu Phe Ala Tyr Phe Ile Arg Asp
```

-continued

```
      240                 245                 250                 255
tgg cgg atg ctg ctg gtg gcg ctg acg atg ccg ggg gtg ctg tgc gtg      936
Trp Arg Met Leu Leu Val Ala Leu Thr Met Pro Gly Val Leu Cys Val
                260                 265                 270 gca ctc tgg tgg ttc atc cct gag tcc ccc cga tgg ctc atc tct cag      984
Ala Leu Trp Trp Phe Ile Pro Glu Ser Pro Arg Trp Leu Ile Ser Gln
            275                 280                 285 gga cga ttt gaa gag gca gag gtg atc atc cgc aag gct gcc aaa gcc     1032
Gly Arg Phe Glu Glu Ala Glu Val Ile Ile Arg Lys Ala Ala Lys Ala
        290                 295                 300 aat ggg att gtt gtg cct tcc act atc ttt gac ccg agt gag tta caa     1080
Asn Gly Ile Val Val Pro Ser Thr Ile Phe Asp Pro Ser Glu Leu Gln
    305                 310                 315 gac cta agt tcc aag aag cag cag tcc cac aac att ctg gat ctg ctt     1128
Asp Leu Ser Ser Lys Lys Gln Gln Ser His Asn Ile Leu Asp Leu Leu
320                 325                 330                 335 cga acc tgg aat atc cgg atg gtc acc atc atg tcc ata atg ctg tgg     1176
Arg Thr Trp Asn Ile Arg Met Val Thr Ile Met Ser Ile Met Leu Trp
                340                 345                 350 atg acc ata tca gtg ggc tat ttt ggg ctt tcg ctt gat act cct aac     1224
Met Thr Ile Ser Val Gly Tyr Phe Gly Leu Ser Leu Asp Thr Pro Asn
            355                 360                 365 ttg cat ggg gac atc ttt gtg aac tgc ttc ctt tca gcg atg gtt gaa     1272
Leu His Gly Asp Ile Phe Val Asn Cys Phe Leu Ser Ala Met Val Glu
        370                 375                 380 gtc cca gca tat gtg ttg gcc tgg ctg ctg ctg caa tat ttg ccc cgg     1320
Val Pro Ala Tyr Val Leu Ala Trp Leu Leu Leu Gln Tyr Leu Pro Arg
    385                 390                 395 cgc tat tcc atg gcc act gcc ctc ttc ctg ggt ggc agt gtc ctt ctc     1368
Arg Tyr Ser Met Ala Thr Ala Leu Phe Leu Gly Gly Ser Val Leu Leu
400                 405                 410                 415 ttc atg cag ctg gta ccc cca gac ttg tat tat ttg gct aca gtc ctg     1416
Phe Met Gln Leu Val Pro Pro Asp Leu Tyr Tyr Leu Ala Thr Val Leu
                420                 425                 430 gtg atg gtg ggc aag ttt gga gtc acg gct gcc ttt tcc atg gtc tac     1464
Val Met Val Gly Lys Phe Gly Val Thr Ala Ala Phe Ser Met Val Tyr
            435                 440                 445 gtg tac aca gcc gag ctg tat ccc aca gtg gtg aga aac atg ggt gtg     1512
Val Tyr Thr Ala Glu Leu Tyr Pro Thr Val Val Arg Asn Met Gly Val
        450                 455                 460 gga gtc agc tcc aca gca tcc cgc ctg ggc agc atc ctg tct ccc tac     1560
Gly Val Ser Ser Thr Ala Ser Arg Leu Gly Ser Ile Leu Ser Pro Tyr
    465                 470                 475 ttc gtt tac ctt ggt gcc tac gac cgc ttc ctg ccc tac att ctc atg     1608
Phe Val Tyr Leu Gly Ala Tyr Asp Arg Phe Leu Pro Tyr Ile Leu Met
480                 485                 490                 495 gga agt ctg acc atc ctg aca gcc atc ctc acc ttg ttt ctc cca gag     1656
Gly Ser Leu Thr Ile Leu Thr Ala Ile Leu Thr Leu Phe Leu Pro Glu
                500                 505                 510 agc ttc ggt acc cca ctc cca gac acc att gac cag atg cta aga gtc     1704
Ser Phe Gly Thr Pro Leu Pro Asp Thr Ile Asp Gln Met Leu Arg Val
            515                 520                 525 aaa gga atg aaa cac aga aaa act cca agt cac aca agg atg tta aaa     1752
Lys Gly Met Lys His Arg Lys Thr Pro Ser His Thr Arg Met Leu Lys
        530                 535                 540 gat ggt caa gaa agg ccc aca atc ctt aaa agc aca gcc ttc             1794
Asp Gly Gln Glu Arg Pro Thr Ile Leu Lys Ser Thr Ala Phe
    545                 550                 555 taacatcgct tccagtaagg gagaaactga agaggaa                             1831
```

```
<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Artificial
      Synthesized Primer Sequence

<400> SEQUENCE: 5
ctaatacgac tcactatagg gc                                          22

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Artificial
      Synthesized Primer Sequence

<400> SEQUENCE: 6
tgtagcgtga agacgacaga a                                           21

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Artificial
      Synthesized Primer Sequence

<400> SEQUENCE: 7
tcgagcggcc gcccgggcag gt                                          22

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Artificial
      Synthesized Primer Sequence

<400> SEQUENCE: 8
agggcgtggt gcggagggcg gt                                          22

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Artificial
      Synthesized Primer Sequence

<400> SEQUENCE: 9
cttttgagca agttcagcct                                             20

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Artificial
      Synthesized Primer Sequence

<400> SEQUENCE: 10
agaggtggct tatgagtatt tctt                                        24
```

```
<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Artificial
      Synthesized Primer Sequence

<400> SEQUENCE: 11
ccagggtttt cccagtcacg ac                                         22

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Artificial
      Synthesized Primer Sequence

<400> SEQUENCE: 12
tcacacagga aacagctatg ac                                         22

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Artificial
      Synthesized Primer Sequence

<400> SEQUENCE: 13
gtgctgttgg gctccttcat ttca                                       24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Artificial
      Synthesized Primer Sequence

<400> SEQUENCE: 14
agctgcatga agagaaggac actg                                       24

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Artificial
      Synthesized Primer Sequence

<400> SEQUENCE: 15
agcatcctgt ctccctactt cgtt                                       24

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence: Artificial
      Synthesized Primer Sequence

<400> SEQUENCE: 16
gatggatccc ggacggtctt gggtcgcctg ctg                             33
```

```
<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence: Artificial
      Synthesized Primer Sequence

<400> SEQUENCE: 17
gatggatcca aatgctgcca catagttgga gat                                      33

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence: Artificial
      Synthesized Primer Sequence

<400> SEQUENCE: 18
gatggatcca tgggcatgca gacaggcttc agc                                      33

<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence: Artificial
      Synthesized Primer Sequence

<400> SEQUENCE: 19
gatggatcct tcctcttcag tttctccctt act                                      33

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Artificial
      Synthesized Primer Sequence

<400> SEQUENCE: 20
cgcgccgaat cgctgaatcc tttc                                                24

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Artificial
      Synthesized Primer Sequence

<400> SEQUENCE: 21
aggcttttga tttgttctgt tgag                                                24

<210> SEQ ID NO 22
<211> LENGTH: 553
<212> TYPE: PRT
<213> ORGANISM: Mus musculus

<400> SEQUENCE: 22

Met Arg Asp Tyr Asp Glu Val Ile Ala Phe Leu Gly Glu Trp Gly Pro
 1               5                  10                  15

Phe Gln Arg Leu Ile Phe Phe Leu Leu Ser Ala Ser Ile Ile Pro Asn
                20                  25                  30

Gly Phe Asn Gly Met Ser Val Val Phe Leu Ala Gly Thr Pro Glu His
```

-continued

```
                 35                  40                  45
Arg Cys Leu Val Pro Asp Thr Val Asn Leu Ser Ser Trp Arg Asn
 50                  55                  60
His Ser Ile Pro Leu Glu Thr Lys Asp Gly Arg Gln Val Pro Gln Ser
 65                  70                  75                  80
Cys Arg Arg Tyr Arg Leu Ala Thr Ile Ala Asn Phe Ser Ala Met Gly
                 85                  90                  95
Leu Glu Pro Gly Gln Asp Val Asp Leu Glu Gln Leu Glu Gln Glu Ser
                100                 105                 110
Cys Leu Asp Gly Trp Glu Tyr Asp Lys Asp Ile Phe Leu Ser Thr Ile
                115                 120                 125
Val Thr Glu Trp Asn Leu Val Cys Glu Asp Asp Trp Lys Thr Pro Leu
130                 135                 140
Thr Thr Ser Leu Phe Phe Val Gly Val Leu Cys Gly Ser Phe Val Ser
145                 150                 155                 160
Gly Gln Leu Ser Asp Arg Phe Gly Arg Lys Lys Val Leu Phe Ala Thr
                165                 170                 175
Met Ala Val Gln Thr Gly Phe Ser Phe Val Gln Ile Phe Ser Thr Asn
                180                 185                 190
Trp Glu Met Phe Thr Val Leu Phe Ala Ile Val Gly Met Gly Gln Ile
                195                 200                 205
Ser Asn Tyr Val Val Ala Phe Ile Leu Gly Thr Glu Ile Leu Ser Lys
210                 215                 220
Ser Val Arg Ile Ile Phe Ser Thr Leu Gly Val Cys Thr Phe Phe Ala
225                 230                 235                 240
Ile Gly Tyr Met Val Leu Pro Leu Phe Ala Tyr Phe Ile Arg Asp Trp
                245                 250                 255
Arg Met Leu Leu Leu Ala Leu Thr Leu Pro Gly Leu Phe Cys Val Pro
                260                 265                 270
Leu Trp Trp Phe Ile Pro Glu Ser Pro Arg Trp Leu Ile Ser Gln Arg
                275                 280                 285
Arg Phe Ala Glu Ala Glu Gln Ile Ile Gln Lys Ala Ala Lys Met Asn
290                 295                 300
Ser Ile Val Ala Pro Ala Gly Ile Phe Asp Pro Leu Glu Leu Gln Glu
305                 310                 315                 320
Leu Asn Ser Leu Lys Gln Gln Lys Val Ile Ile Leu Asp Leu Phe Arg
                325                 330                 335
Thr Arg Asn Ile Ala Thr Ile Thr Val Met Ala Val Met Leu Trp Met
                340                 345                 350
Leu Thr Ser Val Gly Tyr Phe Ala Leu Ser Leu Asn Val Pro Asn Leu
                355                 360                 365
His Gly Asp Val Tyr Leu Asn Cys Phe Leu Ser Gly Leu Ile Glu Val
                370                 375                 380
Pro Ala Tyr Phe Thr Ala Trp Leu Leu Leu Arg Thr Leu Pro Arg Arg
385                 390                 395                 400
Tyr Ile Ile Ala Gly Val Leu Phe Trp Gly Gly Val Leu Leu Leu
                405                 410                 415
Ile Gln Val Val Pro Glu Asp Tyr Asn Phe Val Ser Ile Gly Leu Val
                420                 425                 430
Met Leu Gly Lys Phe Gly Ile Thr Ser Ala Phe Ser Met Leu Tyr Val
                435                 440                 445
Phe Thr Ala Glu Leu Tyr Pro Thr Leu Val Arg Asn Met Ala Val Gly
450                 455                 460
```

-continued

```
Ile Thr Ser Met Ala Ser Arg Val Gly Ser Ile Ala Pro Tyr Phe
465                 470                 475                 480

Val Tyr Leu Gly Ala Tyr Asn Arg Leu Leu Pro Tyr Ile Leu Met Gly
                485                 490                 495

Ser Leu Thr Val Leu Ile Gly Ile Ile Thr Leu Phe Phe Pro Glu Ser
            500                 505                 510

Phe Gly Val Thr Leu Pro Glu Asn Leu Glu Gln Met Gln Lys Val Arg
        515                 520                 525

Gly Phe Arg Cys Gly Lys Lys Ser Thr Val Ser Val Asp Arg Glu Glu
    530                 535                 540

Ser Pro Lys Val Leu Ile Thr Ala Phe
545                 550
```

<210> SEQ ID NO 23
<211> LENGTH: 2083
<212> TYPE: DNA
<213> ORGANISM: Mus musculus
<220> FEATURE:
<221> NAME/KEY: CDS
<222> LOCATION: (122)..(1780)

<400> SEQUENCE: 23

```
attcggcaca ggacggcgtg tttgacgagc cacctaggaa gatcccctca gcgcgccgaa      60
tcgctgaatc ctttctctcc acccacctcc ctcacgcaag ctgaggagga gaggtggaaa     120 c atg cgg gac tac gac gag gtg atc gcc ttc ctg ggc gag tgg ggg ccc    169
  Met Arg Asp Tyr Asp Glu Val Ile Ala Phe Leu Gly Glu Trp Gly Pro
  1               5                   10                  15 ttc cag cgc ctc atc ttc ttt ctg ctc agc gcc agc atc atc ccc aat      217
Phe Gln Arg Leu Ile Phe Phe Leu Leu Ser Ala Ser Ile Ile Pro Asn
                20                  25                  30 ggc ttc aat ggt atg tca gtc gtg ttc ctg gcg ggg acc ccc gag cac      265
Gly Phe Asn Gly Met Ser Val Val Phe Leu Ala Gly Thr Pro Glu His
            35                  40                  45 cgt tgc ctg gtt cct gac act gtg aac ctg agc agc tcc tgg cgc aac      313
Arg Cys Leu Val Pro Asp Thr Val Asn Leu Ser Ser Ser Trp Arg Asn
        50                  55                  60 cac agc atc ccc ttg gag acg aag gac gga cga cag gtg cct cag agc      361
His Ser Ile Pro Leu Glu Thr Lys Asp Gly Arg Gln Val Pro Gln Ser
65                  70                  75                  80 tgc cgc gcc tac cga ctg gcc acc atc gcc aac ttc tct gcg atg ggg      409
Cys Arg Arg Tyr Arg Leu Ala Thr Ile Ala Asn Phe Ser Ala Met Gly
                85                  90                  95 ctg gag cca gga cag gac gtg gat ctg gag cag ctg gag cag gag agc      457
Leu Glu Pro Gly Gln Asp Val Asp Leu Glu Gln Leu Glu Gln Glu Ser
                100                 105                 110 tgc ctg gat ggc tgg gag tac gac aag gac atc ttc ctg tcc acc atc      505
Cys Leu Asp Gly Trp Glu Tyr Asp Lys Asp Ile Phe Leu Ser Thr Ile
            115                 120                 125 gtg aca gag tgg aat ctg gtg tgt gag gat gac tgg aag aca ccc ctc      553
Val Thr Glu Trp Asn Leu Val Cys Glu Asp Asp Trp Lys Thr Pro Leu
        130                 135                 140 acc acc tcc ctg ttc ttc gta ggc gtt ctc tgc ggc tcc ttc gtg tct      601
Thr Thr Ser Leu Phe Phe Val Gly Val Leu Cys Gly Ser Phe Val Ser
145                 150                 155                 160 ggg cag ctg tca gac agg ttt ggc agg aag aaa gtc ctc ttt gca acc      649
Gly Gln Leu Ser Asp Arg Phe Gly Arg Lys Lys Val Leu Phe Ala Thr
                165                 170                 175 atg gct gtg cag act gga ttc agc ttc gtg cag att ttc tca acc aac      697
```

-continued

```
        Met Ala Val Gln Thr Gly Phe Ser Phe Val Gln Ile Phe Ser Thr Asn
                        180                 185                 190 tgg gag atg ttc act gtg ttg ttt gcc att gtg ggc atg ggc cag atc      745
Trp Glu Met Phe Thr Val Leu Phe Ala Ile Val Gly Met Gly Gln Ile
                195                 200                 205 tcc aac tac gtg gtg gcc ttc ata cta gga act gaa atc ctg agc aag      793
Ser Asn Tyr Val Val Ala Phe Ile Leu Gly Thr Glu Ile Leu Ser Lys
            210                 215                 220 tcg gtt cgc atc atc ttc tcc aca tta gga gtc tgt aca ttt ttt gca      841
Ser Val Arg Ile Ile Phe Ser Thr Leu Gly Val Cys Thr Phe Phe Ala
225                 230                 235                 240 atc ggc tac atg gtc ctg ccg ctg ttt gca tac ttc atc aga gac tgg      889
Ile Gly Tyr Met Val Leu Pro Leu Phe Ala Tyr Phe Ile Arg Asp Trp
                245                 250                 255 agg atg ctg ctg ctg gcc ctg aca ctg cct ggc ctg ttc tgt gtt ccc      937
Arg Met Leu Leu Leu Ala Leu Thr Leu Pro Gly Leu Phe Cys Val Pro
            260                 265                 270 ctg tgg tgg ttt att cca gaa tct ccc cgg tgg ctg ata tcc cag agg      985
Leu Trp Trp Phe Ile Pro Glu Ser Pro Arg Trp Leu Ile Ser Gln Arg
        275                 280                 285 aga ttt gca gag gcc gaa cag atc atc cag aaa gcc gca aag atg aac     1033
Arg Phe Ala Glu Ala Glu Gln Ile Ile Gln Lys Ala Ala Lys Met Asn
        290                 295                 300 agc atc gtg gcg cca gca ggg ata ttc gat cct cta gag cta cag gag     1081
Ser Ile Val Ala Pro Ala Gly Ile Phe Asp Pro Leu Glu Leu Gln Glu
305                 310                 315                 320 cta aac tcc ttg aag cag cag aaa gtc ata atc ctg gac ctg ttc agg     1129
Leu Asn Ser Leu Lys Gln Gln Lys Val Ile Ile Leu Asp Leu Phe Arg
                325                 330                 335 act cgg aac att gcc acc ata acc gtg atg gct gtg atg ctg tgg atg     1177
Thr Arg Asn Ile Ala Thr Ile Thr Val Met Ala Val Met Leu Trp Met
            340                 345                 350 cta acc tca gtg ggt tac ttt gct ctg tct ctc aat gtt cct aat tta     1225
Leu Thr Ser Val Gly Tyr Phe Ala Leu Ser Leu Asn Val Pro Asn Leu
        355                 360                 365 cat gga gat gtc tac ctg aac tgc ttc ctc tct ggc ctg att gaa gtt     1273
His Gly Asp Val Tyr Leu Asn Cys Phe Leu Ser Gly Leu Ile Glu Val
370                 375                 380 cca gct tac ttc aca gcc tgg ctg cta ctg cga acc ctg cca cgg aga     1321
Pro Ala Tyr Phe Thr Ala Trp Leu Leu Leu Arg Thr Leu Pro Arg Arg
385                 390                 395                 400 tat att ata gct ggg gtg cta ttc tgg gga gga ggt gtg ctt ctc ttg     1369
Tyr Ile Ile Ala Gly Val Leu Phe Trp Gly Gly Gly Val Leu Leu Leu
                405                 410                 415 atc caa gtg gta cct gaa gat tat aac ttt gtg tcc att gga ctg gtg     1417
Ile Gln Val Val Pro Glu Asp Tyr Asn Phe Val Ser Ile Gly Leu Val
            420                 425                 430 atg ctg ggg aaa ttt ggg atc acc tct gcc ttc tcc atg ttg tat gtc     1465
Met Leu Gly Lys Phe Gly Ile Thr Ser Ala Phe Ser Met Leu Tyr Val
        435                 440                 445 ttc act gcg gag ctc tac cca acc ctg gtc agg aac atg gct gtg ggc     1513
Phe Thr Ala Glu Leu Tyr Pro Thr Leu Val Arg Asn Met Ala Val Gly
450                 455                 460 atc acc tcc atg gcc tct cgg gtg ggc agc atc att gcc ccc tat ttc     1561
Ile Thr Ser Met Ala Ser Arg Val Gly Ser Ile Ile Ala Pro Tyr Phe
465                 470                 475                 480 gtt tac ctg ggc gcc tat aac aga ctc cta ccc tac atc ctc atg ggc     1609
Val Tyr Leu Gly Ala Tyr Asn Arg Leu Leu Pro Tyr Ile Leu Met Gly
                485                 490                 495
```

-continued

```
agt ctg act gtc ctc att gga atc atc acg ctt ttt ttc cct gaa agt    1657
Ser Leu Thr Val Leu Ile Gly Ile Ile Thr Leu Phe Phe Pro Glu Ser
        500                 505                 510 ttt gga gtg act cta cca gag aac ttg gag cag atg cag aaa gtg aga    1705
Phe Gly Val Thr Leu Pro Glu Asn Leu Glu Gln Met Gln Lys Val Arg
    515                 520                 525 ggg ttc aga tgt ggg aaa aaa tca aca gtc tca gtg gac aga gaa gaa    1753
Gly Phe Arg Cys Gly Lys Lys Ser Thr Val Ser Val Asp Arg Glu Glu
530                 535                 540 agc ccc aag gtt cta ata act gca ttc taacgaggtt tccaaggcac          1800
Ser Pro Lys Val Leu Ile Thr Ala Phe
545                 550 ttggcaaact gaaaagcaga tgtatacaat gagcagggtg tgatagagca agcctgcaat  1860
cccagcgctc ttggggtgga gacagaagat caggagttca aggtcatcct tggctacagc  1920
aggagtgtaa gaccagcctg tcttaccaca agcaaccctg tctcaacaga acaaatcaaa  1980
agccttttct gctgaaaggg attaacgaaa acaatgagca ccaaactgga cttgtggaga  2040
aatgcacact atctcatgaa ttctgggcca ctcttccaga tgg                   2083

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Artificial
      Synthesized Primer Sequence

<400> SEQUENCE: 24
cccatgccaa caaggacaaa aagc                                         24

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Artificial
      Synthesized Primer Sequence

<400> SEQUENCE: 25
acagaacaga aaagccctca gtca                                         24

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Artificial
      Synthesized Primer Sequence
<400> SEQUENCE: 26 tgttttttcgt gggtgtgctg atgg                                        24

<210> SEQ ID NO 27
<211> LENGTH: 557
<212> TYPE: PRT
<213> ORGANISM: Mus musculus

<400> SEQUENCE: 27

Met Arg Asp Tyr Asp Glu Val Thr Ala Phe Leu Gly Glu Trp Gly Pro
 1               5                  10                  15

Phe Gln Arg Leu Ile Phe Phe Leu Leu Ser Ala Ser Ile Ile Pro Asn
            20                  25                  30

Gly Phe Asn Gly Met Ser Ile Val Phe Leu Ala Gly Thr Pro Glu His
```

```
                35                  40                  45
Arg Cys Leu Val Pro His Thr Val Asn Leu Ser Ser Ala Trp Arg Asn
 50                  55                  60

His Ser Ile Pro Leu Glu Thr Lys Asp Gly Arg Gln Val Pro Gln Lys
 65                  70                  75                  80

Cys Arg Arg Tyr Arg Leu Ala Thr Ile Ala Asn Phe Ser Glu Leu Gly
                 85                  90                  95

Leu Glu Pro Gly Arg Asp Val Asp Leu Glu Gln Leu Glu Gln Glu Ser
                100                 105                 110

Cys Leu Asp Gly Trp Glu Tyr Asp Lys Asp Val Phe Leu Ser Thr Ile
            115                 120                 125

Val Thr Glu Trp Asp Leu Val Cys Lys Asp Asp Trp Lys Ala Pro Leu
    130                 135                 140

Thr Thr Ser Leu Phe Phe Val Gly Val Leu Met Gly Ser Phe Ile Ser
145                 150                 155                 160

Gly Gln Leu Ser Asp Arg Phe Gly Arg Lys Asn Val Leu Phe Leu Thr
                165                 170                 175

Met Gly Met Gln Thr Gly Phe Ser Phe Leu Gln Val Phe Ser Val Asn
            180                 185                 190

Phe Glu Met Phe Thr Val Leu Phe Val Leu Val Gly Met Gly Gln Ile
        195                 200                 205

Ser Asn Tyr Val Ala Ala Phe Val Leu Gly Thr Glu Ile Leu Ser Lys
    210                 215                 220

Ser Ile Arg Ile Ile Phe Ala Thr Leu Gly Val Cys Ile Phe Tyr Ala
225                 230                 235                 240

Phe Gly Phe Met Val Leu Pro Leu Phe Ala Tyr Phe Ile Arg Asp Trp
                245                 250                 255

Arg Met Leu Leu Leu Ala Leu Thr Val Pro Gly Val Leu Cys Gly Ala
            260                 265                 270

Leu Trp Trp Phe Ile Pro Glu Ser Pro Arg Trp Leu Ile Ser Gln Gly
        275                 280                 285

Arg Ile Lys Glu Ala Glu Val Ile Ile Arg Lys Ala Ala Lys Ile Asn
    290                 295                 300

Gly Ile Val Ala Pro Ser Thr Ile Phe Asp Pro Ser Glu Leu Gln Asp
305                 310                 315                 320

Leu Asn Ser Thr Lys Pro Gln Leu His His Ile Tyr Asp Leu Ile Arg
                325                 330                 335

Thr Arg Asn Ile Arg Val Ile Thr Ile Met Ser Ile Ile Leu Trp Leu
            340                 345                 350

Thr Ile Ser Val Gly Tyr Phe Gly Leu Ser Leu Asp Thr Pro Asn Leu
        355                 360                 365

His Gly Asp Ile Tyr Val Asn Cys Phe Leu Leu Ala Val Glu Val
    370                 375                 380

Pro Ala Tyr Val Leu Ala Trp Leu Leu Leu Gln Tyr Leu Pro Arg Arg
385                 390                 395                 400

Tyr Ser Ile Ser Ala Ala Leu Phe Leu Gly Gly Ser Val Leu Leu Phe
                405                 410                 415

Met Gln Leu Val Pro Ser Glu Leu Phe Tyr Leu Ser Thr Ala Leu Val
            420                 425                 430

Met Val Gly Lys Phe Gly Ile Thr Ser Ala Tyr Ser Met Val Tyr Val
        435                 440                 445

Tyr Thr Ala Glu Leu Tyr Pro Thr Val Val Arg Asn Met Gly Val Gly
450                 455                 460
```

```
Val Ser Ser Thr Ala Ser Arg Leu Gly Ser Ile Leu Ser Pro Tyr Phe
465                 470                 475                 480

Val Tyr Leu Gly Ala Tyr Asp Arg Phe Leu Pro Tyr Ile Leu Met Gly
                485                 490                 495

Ser Leu Thr Ile Leu Thr Ala Ile Leu Thr Leu Phe Phe Pro Glu Ser
                500                 505                 510

Phe Gly Val Pro Leu Pro Asp Thr Ile Asp Gln Met Leu Arg Val Lys
            515                 520                 525

Gly Ile Lys Gln Trp Gln Ile Gln Ser Gln Thr Arg Met Gln Lys Asp
        530                 535                 540

Gly Glu Glu Ser Pro Thr Val Leu Lys Ser Thr Ala Phe
545             550                 555

<210> SEQ ID NO 28
<211> LENGTH: 1888
<212> TYPE: DNA
<213> ORGANISM: Mus musculus
<220> FEATURE:
<221> NAME/KEY: CDS
<222> LOCATION: (60)..(1730)

<400> SEQUENCE: 28
ctcccgcgcc acggtgtccc cttattccca tacgggcgct gtgggaggct gaggacggc      59 atg cgg gac tac gac gag gtg acc gcc ttc cta ggc gag tgg ggg ccc     107
Met Arg Asp Tyr Asp Glu Val Thr Ala Phe Leu Gly Glu Trp Gly Pro
  1               5                  10                  15 ttc cag cgc ctc atc ttc ttc ctg ctc agc gcc agc atc atc ccc aat     155
Phe Gln Arg Leu Ile Phe Phe Leu Leu Ser Ala Ser Ile Ile Pro Asn
             20                  25                  30 ggc ttc aat ggt atg tcc atc gtg ttc ctg gcg ggg acc ccg gag cac     203
Gly Phe Asn Gly Met Ser Ile Val Phe Leu Ala Gly Thr Pro Glu His
         35                  40                  45 cgt tgc ctt gtg cct cac acc gtg aac ctg agc agc gcg tgg cgc aac     251
Arg Cys Leu Val Pro His Thr Val Asn Leu Ser Ser Ala Trp Arg Asn
     50                  55                  60 cac agt atc ccg ttg gag acg aag gac gga cga cag gtg cct cag aaa     299
His Ser Ile Pro Leu Glu Thr Lys Asp Gly Arg Gln Val Pro Gln Lys
 65                  70                  75                  80 tgc cgc cgc tac cga ctg gcc acc atc gcc aac ttc tct gag cta ggg     347
Cys Arg Arg Tyr Arg Leu Ala Thr Ile Ala Asn Phe Ser Glu Leu Gly
                 85                  90                  95 ctg gag ccg ggg cgg gac gtg gac ctg gag cag ctg gag cag gag agc     395
Leu Glu Pro Gly Arg Asp Val Asp Leu Glu Gln Leu Glu Gln Glu Ser
            100                 105                 110 tgc ctg gat ggc tgg gag tac gac aag gac gtc ttc ctg tcc acc atc     443
Cys Leu Asp Gly Trp Glu Tyr Asp Lys Asp Val Phe Leu Ser Thr Ile
        115                 120                 125 gtg aca gag tgg gac ctg gtg tgt aag gat gac tgg aaa gcc cca ctc     491
Val Thr Glu Trp Asp Leu Val Cys Lys Asp Asp Trp Lys Ala Pro Leu
    130                 135                 140 acc acc tcc ttg ttt ttc gtg ggt gtg ctg atg ggc tcc ttc att tca     539
Thr Thr Ser Leu Phe Phe Val Gly Val Leu Met Gly Ser Phe Ile Ser
145                 150                 155                 160 gga cag ctc tca gac agg ttt ggt cgc aag aat gtg ctg ttt ttg acc     587
Gly Gln Leu Ser Asp Arg Phe Gly Arg Lys Asn Val Leu Phe Leu Thr
                165                 170                 175 atg ggc atg cag act ggc ttc agc ttc ctg cag gtc ttc tct gtg aac     635
Met Gly Met Gln Thr Gly Phe Ser Phe Leu Gln Val Phe Ser Val Asn
            180                 185                 190
```

```
ttc gag atg ttt aca gtg ctt ttt gtc ctt gtt ggc atg ggt cag atc      683
Phe Glu Met Phe Thr Val Leu Phe Val Leu Val Gly Met Gly Gln Ile
        195                 200                 205 tcc aac tac gtg gca gca ttt gtc ctg gga aca gaa att ctt tcc aag      731
Ser Asn Tyr Val Ala Ala Phe Val Leu Gly Thr Glu Ile Leu Ser Lys
    210                 215                 220 tca att cga att ata ttc gcc acc tta gga gtt tgc ata ttt tat gcg      779
Ser Ile Arg Ile Ile Phe Ala Thr Leu Gly Val Cys Ile Phe Tyr Ala
225                 230                 235                 240 ttt ggc ttc atg gtg ctg cca ctg ttt gca tac ttc atc aga gac tgg      827
Phe Gly Phe Met Val Leu Pro Leu Phe Ala Tyr Phe Ile Arg Asp Trp
                245                 250                 255 agg atg ctg ctg ctg gcg ctc act gtg cca ggg gtg cta tgt ggg gct      875
Arg Met Leu Leu Leu Ala Leu Thr Val Pro Gly Val Leu Cys Gly Ala
        260                 265                 270 ctc tgg tgg ttc atc cct gag tcc cca cga tgg ctc atc tct caa ggc      923
Leu Trp Trp Phe Ile Pro Glu Ser Pro Arg Trp Leu Ile Ser Gln Gly
    275                 280                 285 cga att aaa gag gca gag gtg atc atc cgc aaa gct gcc aaa atc aat      971
Arg Ile Lys Glu Ala Glu Val Ile Ile Arg Lys Ala Ala Lys Ile Asn
290                 295                 300 ggg att gtt gca cct tcc act atc ttc gat cca agt gag tta caa gac     1019
Gly Ile Val Ala Pro Ser Thr Ile Phe Asp Pro Ser Glu Leu Gln Asp
305                 310                 315                 320 tta aat tct acg aag cct cag ttg cac cac att tat gat ctg atc cga     1067
Leu Asn Ser Thr Lys Pro Gln Leu His His Ile Tyr Asp Leu Ile Arg
                325                 330                 335 aca cgg aat atc agg gtc atc acc atc atg tct ata atc ctg tgg ctg     1115
Thr Arg Asn Ile Arg Val Ile Thr Ile Met Ser Ile Ile Leu Trp Leu
        340                 345                 350 acc ata tca gtg ggc tat ttt gga cta tct ctt gac act cct aac ttg     1163
Thr Ile Ser Val Gly Tyr Phe Gly Leu Ser Leu Asp Thr Pro Asn Leu
    355                 360                 365 cat ggg gac atc tat gtg aac tgc ttc cta ctg gcg gct gtt gaa gtc     1211
His Gly Asp Ile Tyr Val Asn Cys Phe Leu Leu Ala Ala Val Glu Val
370                 375                 380 cca gcc tat gtg ctg gcc tgg ctg ttg cag tac ttg ccc cgg cga         1259
Pro Ala Tyr Val Leu Ala Trp Leu Leu Leu Gln Tyr Leu Pro Arg Arg
385                 390                 395                 400 tat tct atc tcg gct gcc ctt ttc ctg ggt ggc agt gtc ctt ctc ttc     1307
Tyr Ser Ile Ser Ala Ala Leu Phe Leu Gly Gly Ser Val Leu Leu Phe
                405                 410                 415 atg cag ctg gtg cct tca gaa ttg ttt tac ttg tcc act gcc ctg gtg     1355
Met Gln Leu Val Pro Ser Glu Leu Phe Tyr Leu Ser Thr Ala Leu Val
        420                 425                 430 atg gtg ggg aag ttt gga atc acc tct gcc tac tcc atg gtc tat gtg     1403
Met Val Gly Lys Phe Gly Ile Thr Ser Ala Tyr Ser Met Val Tyr Val
    435                 440                 445 tac aca gct gag ctg tac ccc act gtg gtc aga aac atg ggt gtg ggg     1451
Tyr Thr Ala Glu Leu Tyr Pro Thr Val Val Arg Asn Met Gly Val Gly
450                 455                 460 gtc agc tcc aca gca tcc cgc ctt ggc agc atc ctg tct ccc tac ttt     1499
Val Ser Ser Thr Ala Ser Arg Leu Gly Ser Ile Leu Ser Pro Tyr Phe
465                 470                 475                 480 gtt tac cta ggt gcc tat gat cgc ttc ctg cct tat att ctc atg gga     1547
Val Tyr Leu Gly Ala Tyr Asp Arg Phe Leu Pro Tyr Ile Leu Met Gly
                485                 490                 495 agt ctg acc atc ctg aca gct atc ctc acc ttg ttc ttc cct gag agc     1595
Ser Leu Thr Ile Leu Thr Ala Ile Leu Thr Leu Phe Phe Pro Glu Ser
```

-continued

```
                   500             505             510
ttt ggt gtc cct ctc cca gat acc att gac cag atg cta agg gtc aaa      1643
Phe Gly Val Pro Leu Pro Asp Thr Ile Asp Gln Met Leu Arg Val Lys
        515                 520                 525 gga ata aaa cag tgg caa atc caa agc cag aca aga atg caa aaa gat      1691
Gly Ile Lys Gln Trp Gln Ile Gln Ser Gln Thr Arg Met Gln Lys Asp
        530                 535                 540 ggt gaa gaa agc cca aca gtc cta aag agc aca gcc ttc taacaccctg       1740
Gly Glu Glu Ser Pro Thr Val Leu Lys Ser Thr Ala Phe
545                 550                 555 tccagaaggc aaaaaactga ttggaaacct tcatgttgtc agaaatgctc tccatgactg    1800
agggcttttc tgttctgtta accttgtgtc taacatgctc atggattggg gcatctgtcc    1860
tggagagtca ccttcctcta gggacacc                                       1888

<210> SEQ ID NO 29
<211> LENGTH: 44
<212> TYPE: DNA
<213> ORGANISM: Artificial Sequence
<220> FEATURE:
<223> OTHER INFORMATION: Description of Artificial Sequence: Artificial
      Synthesized Adapter Sequence

<400> SEQUENCE: 29
ctaatacgac tcactatagg gctcgagcgg ccgcccgggc aggt                     44

<210> SEQ ID NO 30
<211> LENGTH: 43
<212> TYPE: DNA
<213> ORGANISM: Artificial Sequence
<220> FEATURE:
<223> OTHER INFORMATION: Description of Artificial Sequence: Artificial
      Synthesized Adapter Sequencence

<400> SEQUENCE: 30
tgtagcgtga agacgacaga aagggcgtgg tgcggagggc ggt                      43

<210> SEQ ID NO 31
<211> LENGTH: 10
<212> TYPE: DNA
<213> ORGANISM: Artificial Sequence
<220> FEATURE:
<223> OTHER INFORMATION: Description of Artificial Sequence: Artificial
      Synthesized Adapter Sequence

<400> SEQUENCE: 31
acctgcccgg                                                           10

<210> SEQ ID NO 32
<211> LENGTH: 11
<212> TYPE: DNA
<213> ORGANISM: Artificial Sequence
<220> FEATURE:
<223> OTHER INFORMATION: Description of Artificial Sequence: Artificial
      Synthesized Adapter Sequence

<400> SEQUENCE: 32
accgccctcc g                                                         11

<210> SEQ ID NO 33
<211> LENGTH: 14
<212> TYPE: PRT
<213> ORGANISM: Artificial Sequence
<220> FEATURE:
<223> OTHER INFORMATION: Exemplary motif
```

-continued

```
<220> FEATURE:
<221> NAME/KEY: VARIANT
<222> LOCATION: 1
<223> OTHER INFORMATION: Xaa = Leu, Ile, Val, Met, Ser, Thr, Ala, or Gly
<220> FEATURE:
<221> NAME/KEY: VARIANT
<222> LOCATION: 2
<223> OTHER INFORMATION: Xaa = Leu, Ile, Val, Met, Phe, Ser, Ala, or Gly
<220> FEATURE:
<221> NAME/KEY: VARIANT
<222> LOCATION: 3, 6, 11-13
<223> OTHER INFORMATION: Xaa = any amino acid
<220> FEATURE:
<221> NAME/KEY: VARIANT
<222> LOCATION: 4
<223> OTHER INFORMATION: Xaa = Leu, Ile, Val, Met, Ser, or Ala
<220> FEATURE:
<221> NAME/KEY: VARIANT
<222> LOCATION: 5
<223> OTHER INFORMATION: Xaa = Asp, or Glu
<220> FEATURE:
<221> NAME/KEY: VARIANT
<222> LOCATION: 7
<223> OTHER INFORMATION: Xaa = Leu, Ile, Val, Met, Phe, Tyr, Trp, or Ala
<220> FEATURE:
<221> NAME/KEY: VARIANT
<222> LOCATION: 10
<223> OTHER INFORMATION: Xaa = Arg, or Lys
<220> FEATURE:
<221> NAME/KEY: VARIANT
<222> LOCATION: 14
<223> OTHER INFORMATION: Xaa = Gly, Ser, Thr, or Ala

<400> SEQUENCE: 33

Xaa Xaa Xaa Xaa Xaa Xaa Xaa Gly Arg Xaa Xaa Xaa Xaa Xaa
 1               5                  10
```

TRANSPORTER POLYPEPTIDE AND METHOD OF PRODUCING SAME

This application is a continuation-in-part of PCT/JP98/04009 filed Sep. 7, 1998, and claims priority from Japanese Application No. 9/260972, filed Sep. 8, 1997 and Japanese Application No. 10/156660, filed May 20, 1998.

FIELD OF THE INVENTION

The present invention relates to transporters, proteins involved in transport of substances from the outside to the inside of cells or vice versa.

BACKGROUND OF THE INVENTION

Recently, the involvement of various transporters localized on the plasma membrane in the uptake system for nutrients and endogenous substances into cells and their transport mechanisms have been clarified (Tsuji, A. and Tamai, I., Pharm. Res., 13, 963–977, 1996). These transporters recognize the structures of substances to be transported to selectively transport specific substances. Transporters that recognize the relatively wide range of structures may possibly recognize foreign substances such as drugs by mistake, and actively take in them into cells. It is believed that drugs permeate through the plasma membrane fundamentally by simple diffusion depending on their physico-chemical properties such as molecular size, hydrophobicity, and hydrogen-binding capacity. Particularly, in the case of ionic drugs, only molecules in the non-dissociated form can permeate through the plasma membrane according to the pH partition hypothesis. However, it has become evident that a number of drugs penetrate through the cell membrane by a specific mechanism other than simple diffusion, that is, an active transport mediated by transporters, in organs that require efficient exchange of intracellular and extracellular substances, including small intestine, uriniferous tubule, placenta, epithelial cells of choroid plexus, hepatocytes, and blood-brain barrier (Tamai, I. and Tsuji, A., Pharmacia, 31, 493–497, 1995; Saito, H. and Inui, K., Igaku no Ayumi, 179, 393–397, 1996; Tamai, I., Yakubutsu Dotai (Pharmacokinetics), 11, 642–650, 1996). For example, it is known that although oral β-lactam antibiotics of the non-esterified type are amphoteric or negatively charged in physiological pHs and sparingly soluble in fat, they are readily absorbed through the intestine. The transport study using the isolated membrane-vesicles system demonstrated that an $H^+$-driven peptide transporter localized on the brush-border is involved in the absorption process of these drugs (Tsuji, A. et al., J. Pharmacol. Exp. Ther., 241, 594–601, 1987). Although the specificity of a peptide transport system in terms of the peptide size is so strict as to recognize di- or tri-peptides but not tetrapeptides or larger peptides, it has a rather broad substrate specificity to recognize peptides comprising non-natural amino acids. The peptide transporter mediates transport of β-lactam antibiotics mistakenly due to its broad substrate specificity. This property has been unexpectedly utilized in the clinical field (Tsuji, A., American Chemical Society (eds. Taylor, M. D., Amidon, G. L.), Washington, D.C., 101–134, 1995). Furthermore, a possibility that a transporter is also involved in permeation of substances with a high hydrophobicity such as fatty acids through the plasma membrane has been reported (Schaffer, J. and Lodish, H., Cell, 79, 427–436, 1994).

Since various transporters are supposed to be distributed in organs and cells based on the physiological roles of the organs and cells, their distribution and functions may be specific to organs. Therefore, transporters are expected to be used to impart an organ specificity to pharmacokinetics. In other words, an organ-specific drug delivery system (DDS) can be constructed utilizing transporters. If drug absorption solely relied on simple diffusion is improved by elevating its hydrophobicity, an effect of the drug obtained in the initial transport in the liver can be enhanced and the drug can non-specifically translocates into any organ. In addition, it would also be possible to increase the drug absorption independently of its fat-solubility by designing the drug utilizing the substrate specificity of transporters (Hayashi, K. et al., Drug Delivery System, 11, 205–213, 1996). For this purpose, it is necessary to identify various transporters at the molecular level and analyze their properties in detail. However, their molecular level identification are greatly behind studies on their membrane physiology because they are difficult to handle biochemically and require complicated processes in their functional assays.

Recently, cDNAs of several transporters have been cloned by the expression cloning method using Xenopus oocytes, a foreign gene expression system, and structural homology among them has been revealed (Fei, Y.-J. et al., Nature, 368, 563–566, 1994). For example, Koepsell et al. cloned an organic cation transporter, OCT1, which is assumed to be localized on a basement membrane, using the expression cloning method in 1994 (Grundemann, D. et al., Nature, 372, 549–552, 1994). Subsequently, OCT2 was identified by homology cloning based on the sequence of OCT1 (Okuda, M. et al., Biochem. Biophys. Res. Commun., 224, 500–507, 1996). OCT1 and OCT2 show homology as high as 67% to each other (Grundemann, D. et al., J. Biol. Chem., 272, 10408–10413, 1997). Both of them are intensely expressed in the kidney, but differ in the organ distribution; OCT1 is also expressed in the liver, colon, and small intestine, while OCT2 expression is specific to the kidney.

Only a few reports on identification of transporters at the molecular level, including the reports, are available, and there would be many unknown transporters that may be clinically useful.

SUMMARY OF THE INVENTION

An object of this invention is to provide a family of novel transporter genes, proteins encoded by these genes, and their use.

The present inventors have screened a fetal gene library constructed using the subtractive method by random sequencing based on a working hypothesis that fetal genes include those which are involved in various disorders including cancer and are specifically or intensely expressed in fetal tissues. The inventors discovered an unknown gene showing a significant homology with those for organic cation transporters, OCT1 and OCT2, and attempted to isolate this gene, which was assumed to encode a novel transporter. Thus, the inventors succeeded in isolating the desired gene by screening a cDNA library derived from human fetus. Furthermore, the inventors studied the transporter activity of a protein encoded by the isolated human gene and found that the protein, in fact, functioned as a transporter for various organic cations. The inventors also succeeded in isolating a mouse gene corresponding to the isolated human gene.

This invention relates to a family of novel transporter genes, proteins encoded by these genes, and their use, and more specifically to:

(1) a protein comprising an amino acid sequence set forth in SEQ ID NOs: 1, 3, 22, or 27, or a protein comprising said amino acid sequence in which one or more amino acid residues are substituted, deleted, or added, and having an activity to transport an organic cation;

(2) a protein encoded by a DNA hybridizing to a DNA comprising nucleotide sequence according to SEQ ID NOs: 2, 4, 23, or 28, and having an activity to transport an organic cation;

(3) a DNA encoding the protein according to (1) or (2);

(4) a vector comprising the DNA according to (3);

(5) a transformant expressibly carrying the DNA according to (3);

(6) a method for producing the protein according to (1) or (2), the method comprising culturing the transformant according to (5);

(7) an antibody that binds to the protein according to (1) or (2); and (8) a DNA specifically hybridizing to a DNA comprising a nucleotide sequence set forth in SEQ ID NOs: 2, 4, 23, or 28, and consisting of at least 15 nucleotides.

Nucleotide sequences of cDNAs of novel human transporters isolated by the present inventors are shown in SEQ ID NO: 2 (designated as "human OCTN1") and SEQ ID NO: 4 (designated as "human OCTN2"), respectively. Amino acid sequences of proteins encoded by these cDNAs are shown in SEQ ID NO: 1 and SEQ ID NO: 3, respectively. Amino acid sequences of these two proteins included in the transporter proteins of this invention showed such a high overall homology as about 76%, and both of them retained the following consensus sequence which is conserved in various types of transporters including the glucose transporter: [Leu, Ile, Val, Met, Ser, Thr, Ala, Gly]-[Leu, Ile, Val, Met, Phe, Ser, Ala, Gly]-Xaa<2>-[Leu, Ile, Val, Met, Ser, Ala]-[Asp, Glu]-Xaa-[Leu, Ile, Val, Met, Phe, Tyr, Trp, Ala]-Gly-Arg-[Arg, Lys]-Xaa<4-6>-[Gly, Ser, Thr, Ala] (Maiden, M. C. et al., Nature, 325, 641–643, 1987). In fact, these proteins have an activity to transport various organic cations (see Examples 6 to 8).

The present inventors also isolated mouse genes corresponding to the above-described human OCTN1 and human OCTN2. Nucleotide sequences of the isolated cDNAs are shown in SEQ ID NO: 23 (designated as "mouse OCTN1") and SEQ ID NO: 28 (designated as "mouse OCTN2"), respectively. Amino acid sequences of proteins encoded by these cDNAs are shown in SEQ ID NOs: 22 and 27, respectively.

Transporter proteins of this invention also include those having the additional activity to transport substances other than organic cations as far as they retain the organic cation transport activity. Organic cations include, for example, TEA, carnitine, quinidine, and pyrilamine, but are not limited to them. They also include carcinostatic agents such as actinomycin D, etoposide, vinblastine, daunomycin, etc. Transporter proteins of this invention include those having the activity to transport organic cations not only from the outside to the inside of cells but also from the inside to the outside of cells.

Transporter proteins of this invention can be prepared as recombinant proteins using recombination techniques or natural proteins. Recombinant proteins can be prepared, for example, as described below, by culturing cells transformed with DNA encoding proteins of this invention. Natural proteins can be isolated from the kidney and cancer cell strains such as Hela S3, which highly express the proteins of this invention, by the method well known to those skilled in the art, for example, affinity chromatography using an antibody of this invention described below. The antibody may be either polyclonal or monoclonal. A polyclonal antibody can be prepared by purifying serum obtained from, for example, a small animal such as a rabbit immunized with proteins of this invention by known methods, for example, ammonium sulfate precipitation, protein A or protein G column, DEAE-ion exchange column chromatography, affinity column chromatography coupled with the protein of this invention, etc. A monoclonal antibody can be prepared by immunizing a small animal such as a mouse with the protein of this invention, excising the spleen from the mouse, grinding the tissue into cells, fusing them with mouse myeloma cells using a fusing agent such as polyethylene glycol, and selecting a clone that produces an antibody to proteins of this invention out of fused cells (hybridomas) thus produced. Then, hybridomas thus selected are transplanted into the abdominal cavity of a mouse, and the ascites is collected from the mouse. A monoclonal antibody thus obtained can be purified by, for example, ammonium sulfate precipitation, protein A or protein G column, DEAE-ion exchange column chromatography, affinity column chromatography coupled with the protein of this invention, etc. When the antibody thus obtained is administered to human subjects, a humanized antibody or a human antibody is advantageously used to reduce the immunogenicity. An antibody can be humanized by, for example, the CDR grafting method comprising cloning an antibody gene from monoclonal antibody-producing cells and grafting the epitope portion thereof into an existing human antibody. A human antibody can be prepared by the usual method for preparing a monoclonal antibody except for immunizing a mouse whose immune system is replaced with the human's.

The term "substantially pure" as used herein in reference to a given polypeptide means that the polypeptide is substantially free from other biological macromolecules. The substantially pure polypeptide is at least 75% (e.g., at least 80, 85, 95, or 99%) pure by dry weight. Purity can be measured by any appropriate standard method, for example, by column chromatography, polyacrylamide gel electrophoresis, or HPLC analysis.

A "conservative amino acid substitution" is one in which an amino acid residue is replaced with another residue having a chemically similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

It is also possible for those skilled in the art to prepare proteins having functions equivalent to the transporter proteins of this invention (human OCTN1, human OCTN2, mouse OCTN1, and mouse OCTN2) by appropriately modifying amino acid residues of the proteins by, for example, substitution, using well known methods. Mutation of amino acids of the proteins can occur also spontaneously. Such mutant proteins which are obtained by altering the amino acid sequence of the transporter proteins of this invention by substitution, deletion, or addition of amino acid residues, and are functionally equivalent to those of the transporter proteins are also included in the proteins of this invention. Herein, "functionally equivalent" means that proteins have an activity to transport organic cations. Methods well known to those skilled in the art for altering amino acids include, for example, the site-specific mutagenesis system by PCR (GIBCO-BRL, Gaithersburg, Md.), site-specific mutagenesis by oligonucleotide (Kramer, W. and Fritz, H. J. (1987) Methods in Enzymol., 154: 350–367), Kunkel's method (Methods Enzymol., 85, 2763–2766 (1988)), etc. The number of amino acids that can be substituted is usually 10 amino acid residues or less, preferably 6 or less, and more preferably 3 or less. The site of substitution, deletion, or addition of amino acid residues is not particularly limited as far as the activity of proteins of this invention is retained. It is possible to detect the transporter activity of proteins, for example, by the method described below in Example 6.

It is routine for those skilled in the art to obtain proteins functionally equivalent to the transporter proteins of this invention by isolating and using DNAs highly homologous to the DNA sequences encoding the transporter proteins of this invention (human OCTN1, human OCTN2, mouse OCTN1, and mouse OCTN2) or portions thereof using hybridization techniques (Sambrook, J. et al., Molecular Cloning 2nd ed., 9.47–9.58, Cold Spring Harbor Lab. press, 1989), etc. These proteins functionally equivalent to those of transporter proteins of this invention are also included in proteins of this invention. Here, "functionally equivalent" means that proteins have an activity to transport organic cations. DNAs that hybridize to the DNAs encoding the proteins of this invention can be isolated from other organisms, for example, rats, rabbits, cattle, etc. as well as humans and mice. Especially, tissues such as the kidney are suitable as sources of such DNAs. These DNAs isolated using hybridization techniques usually have a high homology with the above-described DNAs encoding the transporter proteins of this invention. "High homology" means at least 70% or more, preferably at least 80% or more, and more preferably at least 90% or more of amino acid sequence identity. The "percent identity" of two amino acid sequences or of two nucleic acids is determined using the algorithm of Karlin and Altschul (Proc. Natl. Acad. Sci. USA 87:2264–2268, 1990), modified as in Karlin and Altschul (Proc. Natl. Acad. Sci. USA 90:5873–5877, 1993). Such an algorithm is incorporated into the NBLAST and XBLAST programs of Altschul et al. (J. Mol. Biol. 215:403–410, 1990). BLAST nucleotide searches are performed with the NBLAST program, score=100, wordlength=12. BLAST protein searches are performed with the XBLAST program, score=50, wordlength=3. Where gaps exist between two sequences, Gapped BLAST is utilized as described in Altschul et al. (Nucleic Acids Res. 25:3389–3402, 1997). When utilizing BLAST and Gapped BLAST programs, the default parameters of the respective programs (e.g., XBLAST and NBLAST) are used. See http://www.ncbi.nlm.nih.gov.

One example of hybridization conditions for isolating such DNAs is as follows. That is, after the pre-hybridization at 55° C. for 30 min or more in the "ExpressHyb Hybridization Solution" (CLONTECH), a labeled probe is added, and hybridization is performed by heating the reaction mixture at 3° C. to 55° C. for 1 h or more. Then, the reaction product is successively washed in 2×SSC and 0.1% SDS three times at room temperature for 20 min, and then in 1×SSC and 0.1% SDS once at 37° C. for 20 min. More preferable conditions are as follows. After the pre-hybridization at 60° C. for 30 min or more in the "ExpressHyb Hybridization Solution" (CLONTECH), a labeled probe is added, and hybridization is performed by heating the reaction mixture at 60° C. for 1 h or more. Then, the reaction product is successively washed in 2×SSC and 0.1% SDS three times at room temperature for 20 min, and then in 1×SSC and 0.1% SDS twice at 50° C. for 20 min. Still more preferable conditions are as follows. After pre-hybridization at 68° C. for 30 min or more in the "ExpressHyb Hybridization Solution" (CLONTECH), a labeled probe is added, and hybridization is performed by heating the reaction mixture at 68° C. for 1 h or more. Then, the reaction product is successively washed in 2×SSC and 0.1% SDS three times at room temperature for 20 min, and then in 0.1×SSC and 0.1% SDS twice at 50° C. for 20 min.

The present invention also relates to DNAs encoding the above-described transporter proteins of this invention. DNAs of this invention may be cDNA, genomic DNAs, and synthetic DNAs. The DNAs of the present invention can be used for producing proteins of this invention as recombinant proteins. That is, it is possible to prepare proteins of this invention as recombinant proteins by inserting DNAs encoding proteins of this invention (e.g. DNAs comprising the nucleotide sequences set forth in SEQ ID NOs: 2, 4, 23, and 28) into an appropriate expression vector, culturing transformants obtained by transfecting suitable cells with the vector, and purifying the proteins thus expressed. Cells to be used for producing recombinant proteins include, for example, mammalian cells such as COS cells, CHO cells, NIH3T3 cells, etc., insect cells such as Sf9 cells, yeast cells, E. coli, and so on. Vectors used for the intracellular expression of recombinant proteins vary depending on host cells, including, for example, pcDNA3 (Invitrogen), pEF-BOS (Nucleic Acids Res., 1990, 18(7), p5322), etc. for mammalian cells, "BAC-to-BAC baculovirus expression system" (GIBCO BRL), etc. for insect cells, "Pichia Expression Kit" (Invitrogen), etc. for yeast cells, pGEX-5X-1 (Pharmacia), "QIAexpress system" (Qiagen), etc. for E. coli. Host cells can be transformed with vectors, for example, by the calcium phosphate method, the DEAE-dextran method, the method using cationic liposome DOTAP (Boehringer Mannheim), the electroporation method, the calcium chloride method, etc. Recombinant proteins can be purified from recombinants thus obtained using standard methods, for example, as described in "The Qiaexpressionist Handbook, Qiagen, Hilden, Germany."

The present invention also relates to DNAs consisting of at least 15 nucleotides that specifically hybridize to the DNAs encoding proteins of this invention. Herein, "specifically hybridize" means that a DNA does not cross-hybridize to other DNAs encoding other proteins under usual hybridization conditions, preferably under the stringent hybridization conditions. Such a DNA can be utilized as a probe for detecting and isolating DNA encoding the protein of this invention, and as a primer for amplifying the DNA.

By hybridization under "stringent conditions" is meant hybridization at 37° C., 1×SSC, followed by washing at 42° C., 0.5×SSC.

An "isolated nucleic acid" is a nucleic acid the structure of which is not identical to that of any naturally occurring nucleic acid or to that of any fragment of a naturally occurring genomic nucleic acid spanning more than three separate genes. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of different (i) DNA molecules, (ii) transfected cells, or (iii) cell clones: e.g., as these occur in a DNA library such as a cDNA or genomic DNA library.

The transporter proteins of this invention can be used to control internal absorption and dynamics of drugs. Based on the results of detailed analysis of the substrate specificity of transporter proteins of this invention, drugs can be designed so as to be transported by these transporters and absorbability of the drugs mediated by these transporter proteins can be improved. Conventional modifications to enhance hydrophobicity are no longer necessary for drugs so designed, which enables speedily and efficiently developing water-soluble drugs that are easy to handle. The drugs thus developed is thought to be absorbed principally depending on the internal distribution pattern of transporter proteins of this invention, and an organ-specific delivery of the drugs thus becomes possible. Especially, if the transporter proteins of this invention are distributed in the target organ of a drug, an ideal drug delivery system (DDS) can be developed. If a drug is to be absorbed mediated by not the transporter proteins of this invention but other transporters, the drug can be designed so as to be specific to other transporter proteins by designing it considering the substrate specificity of the transporter proteins of this invention. Since the transporter proteins of this invention are present in the kidney, it is possible to reduce the nephrotoxicity produced by a drug by designing the drug so that it can be readily excreted by the transporter proteins of this invention.

Another possible application of this invention is to develop a drug targeting the transporter proteins of this invention. The transporters play important roles in the absorption mechanism of nutrients and drugs, or the excretion mechanism of drugs and internal metabolites. Thus, damage or abnormal elevation of the transporter's functions may cause some disorders. It is considered to be efficacious against such disorders to administer a drug containing a compound that inhibits or enhances functions of the transporter proteins of this invention, or regulates the expression level of the transporter gene of this invention and the amount of the transporter proteins. The DNAs of this invention can be used in gene therapy for disorders caused by abnormalities in the activity and expression of the proteins of this invention. In this case, the DNA of this invention are inserted to an adenovirus vector (e.g. pAdexLcw), a retrovirus vector (e.g. pZIPneo), etc., and administered into the body by either ex vivo method or in vivo method. Gene therapy can also be performed by administering a synthetic antisense DNA to the body either directly or after inserted into the above-described vector.

Especially, since "OCTN2" included in the transporter proteins of this invention efficiently transports carnitine, chemotherapy with compounds to control the activity of "OCTN2" or gene therapy using the "OCTN2" gene is considered to be efficacious against various pathological conditions such as fatty liver, myocardiopathy, myopathy, etc. caused by hypocarnitinemia.

The transporter proteins of this invention are expressed in a variety of cancer cell strains, which suggests that the proteins may transport drugs into tumor cells. If this is the case, it is possible to develop carcinostatics that will be readily absorbed mediated by the transporter proteins of this invention. On the contrary, mechanisms to transport and excrete substances by the transporter proteins of this invention may function to excrete carcinostatics in tumor cells so that the cells acquire resistance to drugs. If the transporter proteins of this invention are involved in a mechanism of tumor cells to acquire drug resistance, a carcinostatic effect can be enhanced by a combined use of inhibitors of the transporter proteins of this invention with carcinostatics.

BRIEF DESCRIPTION OF THE DRAWINGS

FIG. 3 compares the amino acid sequence of human OCTN1 (SEQ ID NO:1) with that of human OCTN2 (SEQ ID NO:3). Amino acid residues conserved in both transporters are shaded. Sequences coinciding with the consensus sequences of sugar tansporter and the ATP/GTP binding site are indicated by "+" and "*," respectively.

DETAILED DESCRIPTION

Figure 1:
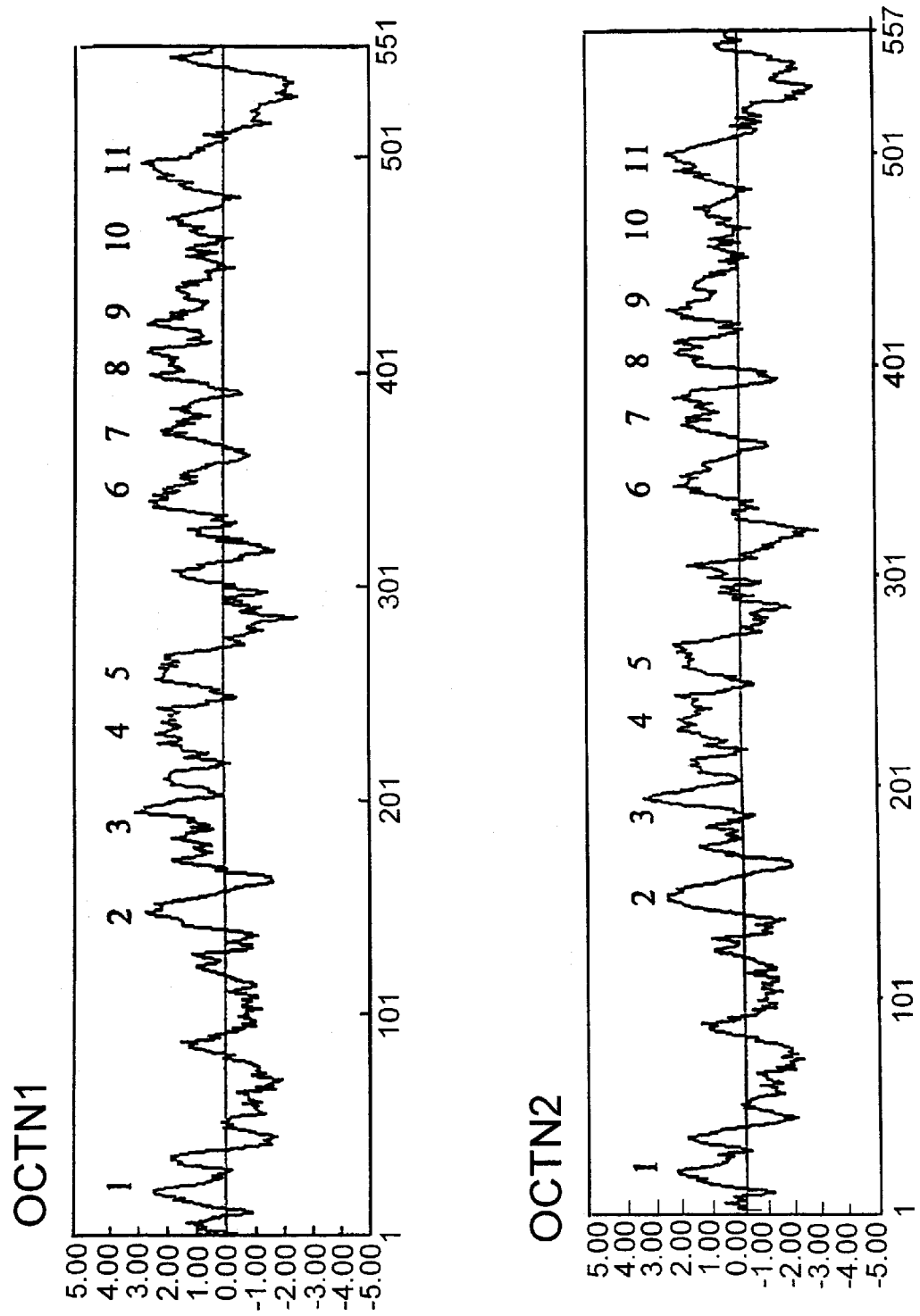
FIG. 1 represents hydrophobicity plots of human OCTN1 and human OCTN2 according to Kyte & Doolittle's calculating formula with a window of nine amino acid residues. Numerals on the plots indicate putative transmembrane regions.

The present invention is described below in more detail with reference to examples, but is not construed being limited thereto.

EXAMPLE 1

Construction of a Subtraction Library

A subtraction library was constructed using the PCR-Select™ cDNA Subtraction Kit (CLONTECH) principally according to the method of Luda Diatchenko (Diatchenko, L. et al., Proc. Natl. Acad. Sci. USA, 93, 6025–6030, 1996).

First, double-stranded cDNAs were synthesized from poly(A)$^+$ RNAs derived from human fetal liver and adult liver by the standard method using MMLV reverse transcriptase. These cDNAs were blunt-ended with T4 DNA polymerase and cleaved with RsaI. A part of the cDNAs derived from fetal liver (tester) was divided in two portions, and they were separately ligated to two different adapters, adapter 1 and adapter 2, respectively (Table 1). A 120-fold excess of cDNA derived from adult liver (driver) was added to each of the above-described tester samples. The mixture was heat-denatured and subjected to the primary hybridization at 68° C. for 8 h. After these two reaction mixtures from the primary hybridization were mixed together without heat-denaturation, an excessive amount of the heat-denatured driver was further added thereto, and the mixture was subjected to the secondary hybridization at 68° C. for about 16 h. The resulting reaction solution was diluted with a dilution buffer and incubated at 75° C. for 7 min. After the shorter strands of adapters were removed, the reaction solution was used as a template for PCR. PCR using primers 1 (5'-CTAATACGACTCACTATAGGGC-3', SEQ ID NO: 5) and 2 (5'-TGTAGCGTGAAGACGACAGAA-3', SEQ ID NO: 6) corresponding to the adapters selectively amplified only cDNA having different adapters at their both ends (subtracted cDNAs)(suppression PCR). PCR was carried out using a portion of the resulting cDNA as a template, and nested PCR primers 1 (5'-TCGAGCGGCCGCCCGGGC AGGT-3', SEQ ID NO: 7) and 2 (5'-AGGGCGTGGTGCG GAGGGCGGT-3', SEQ ID NO: 8), which are further inwardly located from the PCR primers 1 and 2, to obtain products with further elevated selectivity, PCR products thus obtained were purified using the QIAquick PCR Purification kit (QIAGEN), and cloned into the pT7Blue-T vector (Novagen) by the TA cloning method to construct a subtraction library.

EXAMPLE 2 cDNA Cloning

To analyze fetal genes, the subtraction library derived from the fetal liver was screened by random sequencing. Homology search (Blastx) of Expressed Sequence Tags (ESTs) thus obtained found a clone, OCTN1 (fls 631) (292 bp) encoding amino acid sequence having significant homology with the known organic cation transporters, OCT1 (Grundemann, D. et al., Nature, 372, 549–552, 1994) and OCT2 (Okuda, M. et al., Biochem. Biophys. Res. Commun., 224, 500–507, 1996). Since the sequence of this clone was novel and assumed to be a fragment derived from a new transporter gene, cDNA comprising the whole open reading frame (ORF) of this gene was cloned.

The human fetal liver 5'-stretch cDNA library (CLONTECH) was screened using the original OCTN1 clone obtained from the subtraction library derived from fetal liver as a probe. An insert of the original OCTN1 clone was amplified by PCR using M13 P4-22 and M13 P5-22, and labeled with [α-$^{32}$P]dCTP by the random primer method using the Ready-to Go DNA labeling beads (Pharmacia) to serve as a probe. Hybridization was carried out at 68° C. in the ExpressHyb Hybridization Solution (CLONTECH) according to the method recommended by the manufacturer. Final washing was performed at 50° C. in 0.1×SSC and 0.1% SDS. Screening about 5×10$^5$ phage clones finally isolated seven positive clones. cDNA inserts of these clones were amplified by PCR using vector primers designed based on a sequence of the λgt10 vector (GT10 S1 5'-CTTTTGAGCAAGTTCAGCCT-3', SEQ ID NO: 9, and GT10 A1 5'-AGAGGTGGCTTATGAGTATTTCTT-3', SEQ ID NO: 10), or primers designed based on the decoded cDNA sequences. The PCR products thus obtained were directly sequenced to determine the nucleotide sequences. Some regions that were difficult to be amplified were subjected to PCR using 7-deaza dGTP as a substrate base (McConlogue, L. et al., Nucleic Acids Res., 16, 9869, 1988).

Sequencing of cDNA inserts of these clones revealed that the human OCTN1 gene contains an ORF encoding a protein consisting of 551 amino acid residues (putative molecular weight of about 62,000). Data base search using this whole amino acid sequence confirmed that it has a significant overall homology (about 34%) with OCT1 and OCT2. Hydrophobicity profile of this sequence obtained by Kyte & Doolittle's calculating formula (Kyte, J. and Doolittle, R. F., J. Mol. Biol., 157, 105–132, 1982) very closely resembled those of OCT1 and OCT2, indicating that the sequence has eleven to twelve putative transmembrane hydrophobic regions (FIG. 1). This sequence contained one consensus sequence of sugar transporter, ([Leu, Ile, Val, Met, Ser, Thr, Ala, Gly]-[Leu, Ile, Val, Met, Phe, Ser, Ala, Gly]-Xaa<2>-[Leu, Ile, Val, Met, Ser, Ala]-[Asp, Glu]-Xaa-

TABLE 1

```
Adapter 1   5'-CTAATACGACTCACTATAGGGCTCGAGCGGCCGCCCGGGCAGGT-3'
                                              3'-GGCCCGTCCA-5'
Adapter 2   5'-TGTAGCGTGAAGACGACAGAAAGGGCGTGGTGCGGAGGGCGGT-3'
                                              3'-GCCTCCCGCCA-5'
```

The longer strand of the partially single stranded DNA of Adapters 1 and 2 are designated SEQ ID NOs:29 and 30, respectively, and the shorter strand of Adapters 1 and 2 are designated SEQ ID NOs:31 and 32, respectively.

[Leu, Ile, Val, Met, Phe, Tyr, Trp, Ala]-Gly-Arg-[Arg, Lys]-Xaa<4-6>-[Gly, Ser, Thr, Ala]), (160 to 175). This consensus sequence is present in the glucose transporters GLUT1 to GLUT7 in mammalian cells, and also present in various types of transporters other than glucose transporters (Maiden, M. C. et al., Nature, 325, 641–643, 1987). Furthermore, putative N-linked glycosylation sequences (N-X-[ST]) were found in the amino acid sequence of human OCTN1 at four sites (57 to 59, 64 to 66, 91 to 93, and 304 to 306), and also five putative protein kinase C phosphorylation sites ([ST]-X-[RK]) (164 to 166, 225 to 227, 280 to 282, 286 to 288, and 530 to 532). In addition, the consensus sequence ([Ala, Gly]-Xaa(4)-Gly-Lys-[Ser, Thr]) of the ATP/GTP binding site is also found. This consensus sequence of the ATP/GTP binding site is also present in the ATP binding protein or GTP binding protein, such as kinases and ras family proteins, and that ATP or GTP binds to this site (Walker, J. E. et al., EMBO J., 1, 945–951, 1982). This sequence is present in the so-called ATP Binding Cassette (ABC) type transporter, and involved in the substance transport using the energy generated by hydrolysis of ATP (Higgins, C. F. et al., J. Bioenerg. Biomembr., 22, 571–592, 1990; Urbatsch, I. L. et al., J. Biol. Chem., 270, 26956–26961, 1995). Presence of this consensus sequence indicates that OCTN1 protein may be an ATP or GTP-dependent transporter.

Nucleotide sequencing was performed by the cycle-sequencing method with a plasmid DNA prepared by the alkaline-SDS method or a PCR product obtained by colony PCR, etc. as a template using the ABI PRISM™ Dye Terminator Cycle Sequencing Ready Reaction Kit With AmplyTaq DNA Polymerase, FS, followed by decoding with the ABI 377 DNA Sequencer (Perkin Elmer). Colony PCR was carried out by directly suspending a colony of a recombinant in a PCR reaction solution containing vector primers M13 P4-22 (5'-CCAGGGTTTTCCCAGTCACG AC-3', SEQ ID NO: 11) and M13 P5-22 (5'-TCACACA GGAAACAGCTATGAC-3', SEQ ID NO: 12). After the completion of PCR, a DNA insert thus amplified was separated from unreacted primers and nucleotides by gel filtration, etc. to serve as a template for sequencing.

EXAMPLE 3

Northern Analysis

Figure 2:
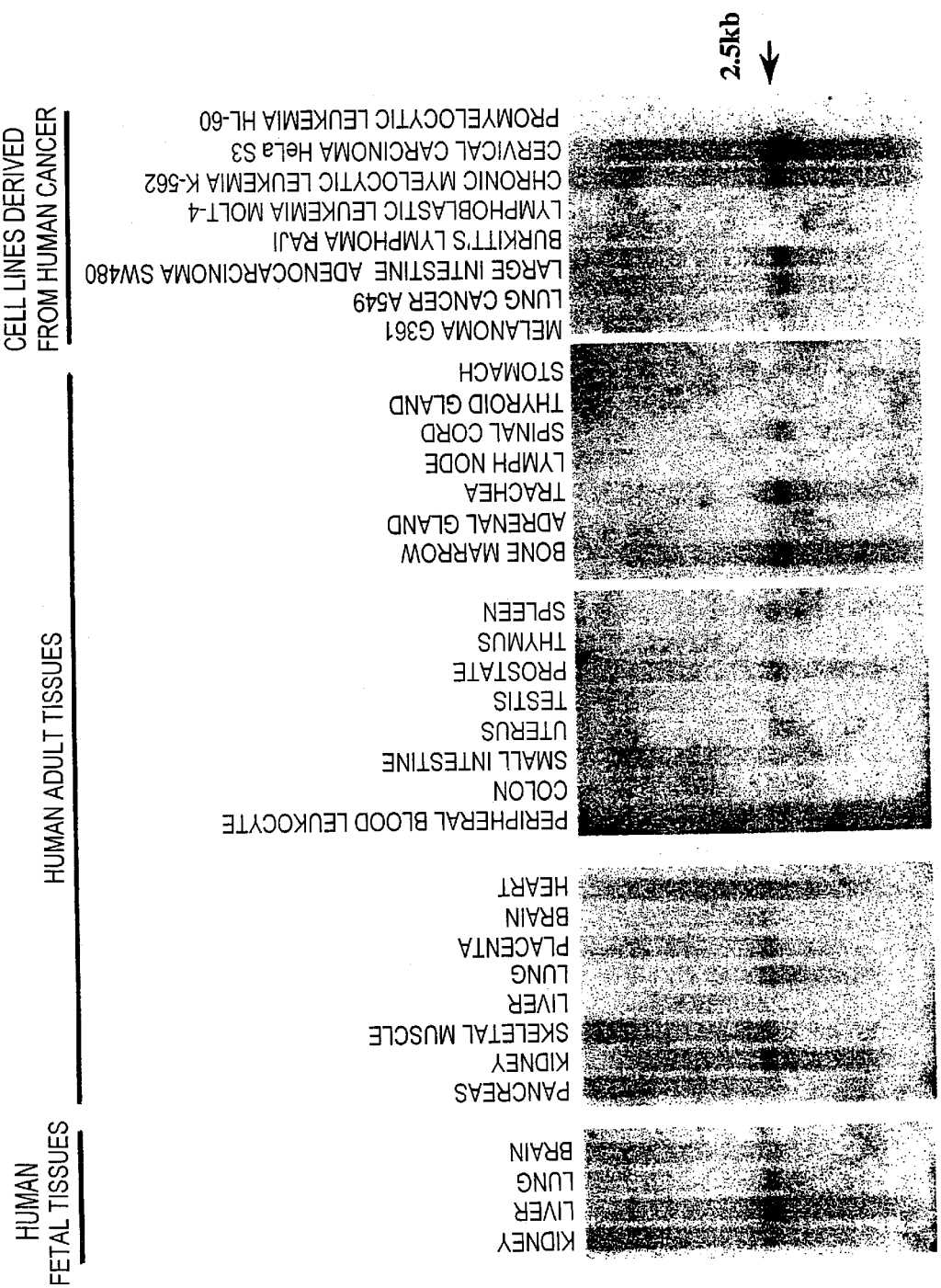
FIG. 2 represents electrophoretic patterns showing the results of Northern blot analysis of human OCTN1.

Distribution of human OCTN1 in tissues was investigated by Northern analysis (FIG. 2). A 3'-end fragment of human OCTN1 (the latter half from around the base 1,100) was labelled with [$\alpha$-$^{32}$P]dCTP by the random primer method using the Ready-to Go DNA labeling beads (Pharmacia) to serve as a probe. Hybridization was performed using the Multiple Tissue Northern (MTN) Blot—Human, Human III, Human IV, Human Fetal II, and Human Cell lines (CLONTECH) at 68° C. in the ExpressHyb Hybridization Solution (CLONTECH) according to the method recommended by the manufacturer. Final washing was performed at 50° C. in 0.1×SSC and 0.1% SDS. As a result, RNA of about 2.5 kb was strongly expressed in the fetal liver and adult-derived tissues such as the kidney, bone marrow, and trachea. Besides those tissues, the RNA band was also weakly detected in the fetal kidney and lung, and adult tissues including skeletal muscle, lung, placenta, prostate, spleen, and spinal cord. The RNA expression was also detected in tumor cell lines such as HeLa S3, K562, SW480, and A549, and especially, its very intense expression was observed in HeLa S3.

EXAMPLE 4

Cloning of Human OCTN2 cDNA

Data base search using the entire nucleotide sequence of "human OCTN1" can detect very similar sequences thereto in several parts of the nucleotide sequence of P1 phage clones (P1 H24 clones, GenBank accession No. L43407, L43408, L46907, L81773, and L43409) derived from q regions of human chromosome 5. The parts having similarity with the nucleotide sequence of human OCTN1 are separated by the sequences having no similarity to the human OCTN1 sequence. The sequence obtained by connecting these similar parts with each other with reference to the sequence of human OCTN1 has a high homology over a wide range with human OCTN1, indicating the presence of OCTN1 homologues. The genomic sequence registered in data base was an incomplete one without covering the entire coding region, and, from only this sequence, it was impossible to know the complete structure of a protein partially encoded by the sequence. Therefore, cDNA cloning of this OCTN1 homologous gene (OCTN2) was performed to determine the coded protein structure. First, 631R S4 primer (5'-GTGCTGTTGGGCTCCTTCATTTCA-3', SEQ ID NO: 13) and 631R A1 primer (5'-AGCTGCATGAAGAGAAG GACACTG-3', SEQ ID NO: 14) were prepared based on sequences of these P1 phage clones. PCR was performed using a set of these primers and cDNA synthesized from poly(A)$^+$ RNA derived from the human adult kidney (CLONTECH) as a template, under the following conditions: 1 cycle of 94° C. for 3 min; 35 cycles of 94° C. for 30 s, 58° C. for 1 min, and 72° C. for 2 min,; and 1 cycle of 72° C. for 10 min, resulting in amplification of about 900 bp fragment. This fragment was subcloned into the pT7Blue-T vector (Novagen) by the TA cloning method to determine its nucleotide sequence, which clearly showed a very high overall homology with human OCTN1. Therefore, this gene was designated as human OCTN2, and longer cDNAs were cloned.

The cDNA library derived from the human kidney was screened using the cDNA insert of this clone as a probe in the same manner as for human OCTN1 cDNA cloning, and cDNA containing the entire coding region of human OCTN2 was cloned by a procedure for isolating longer clone and the Rapid Amplification of cDNA Ends (RACE) method (Chenchik, A., Moqadam, F., and Siebert, P. (1995), CLON-TECHniques X, 5–8), etc. to determine its structure (SEQ ID NO: 4). Specifically, the RACE method was carried out as follows. The 631R S6 primer (5'-AGCATCCTGTCTCC CTACTTCGTT-3', SEQ ID NO: 15) was prepared. PCR was performed using this primer and the Marathon-Ready™ cDNA derived from the human adult kidney (CLONTECH) as a template under the following conditions: 94° C. for 2 min; 35 cycles of 94° C. for 30 s, 60° C. for 1 min, and 72° C. for 3 min,; and 72° C. for 10 min, resulting in amplification of about 1.7 kbp cDNA fragment of the 3'-end. This fragment was subcloned into the pT7Blue-T vector by the TA cloning method to determine its structure.

Figure 3:
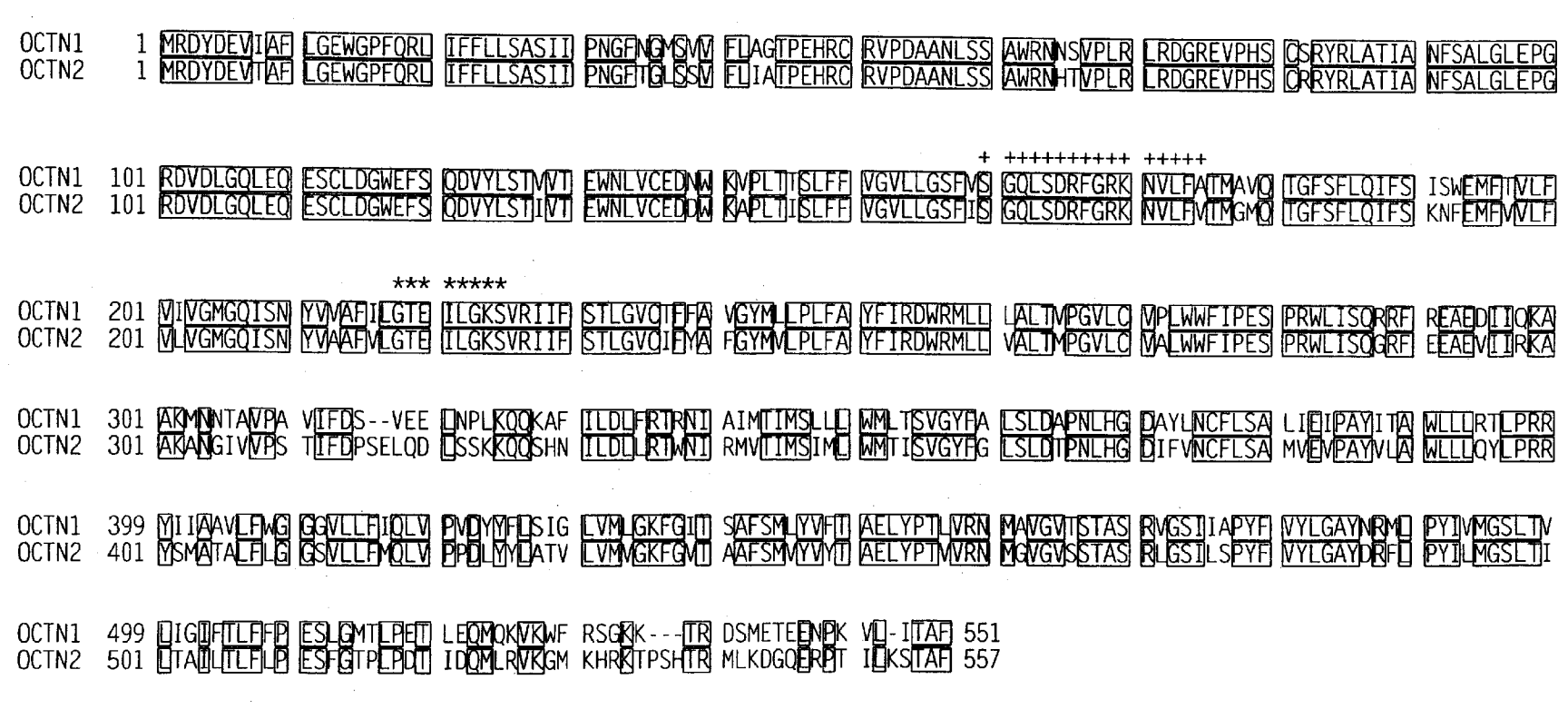

It became evident that human OCTN2 contains an open reading frame (ORP) encoding a protein consisting of 557 amino acid residues. FIG. 3 compares amino acid sequences of human OCTN1 and human OCTN2. Both showed overall amino acid homology as high as about 76%. In addition, one a consensus sequence (160 to 176) of sugar transporter was a present in the amino acid sequence of human OCTN2 like human OCTN1. These facts indicated that human OCTN2 can be a novel transporter that is structurally related to human OCTN1. Furthermore, a consensus sequence (218 to 225) of the ATP/GTP binding site was also present in the amino acid sequence of human OCTN2 like in human OCTN1.

EXAMPLE 5

Northern Analysis

Figure 4:
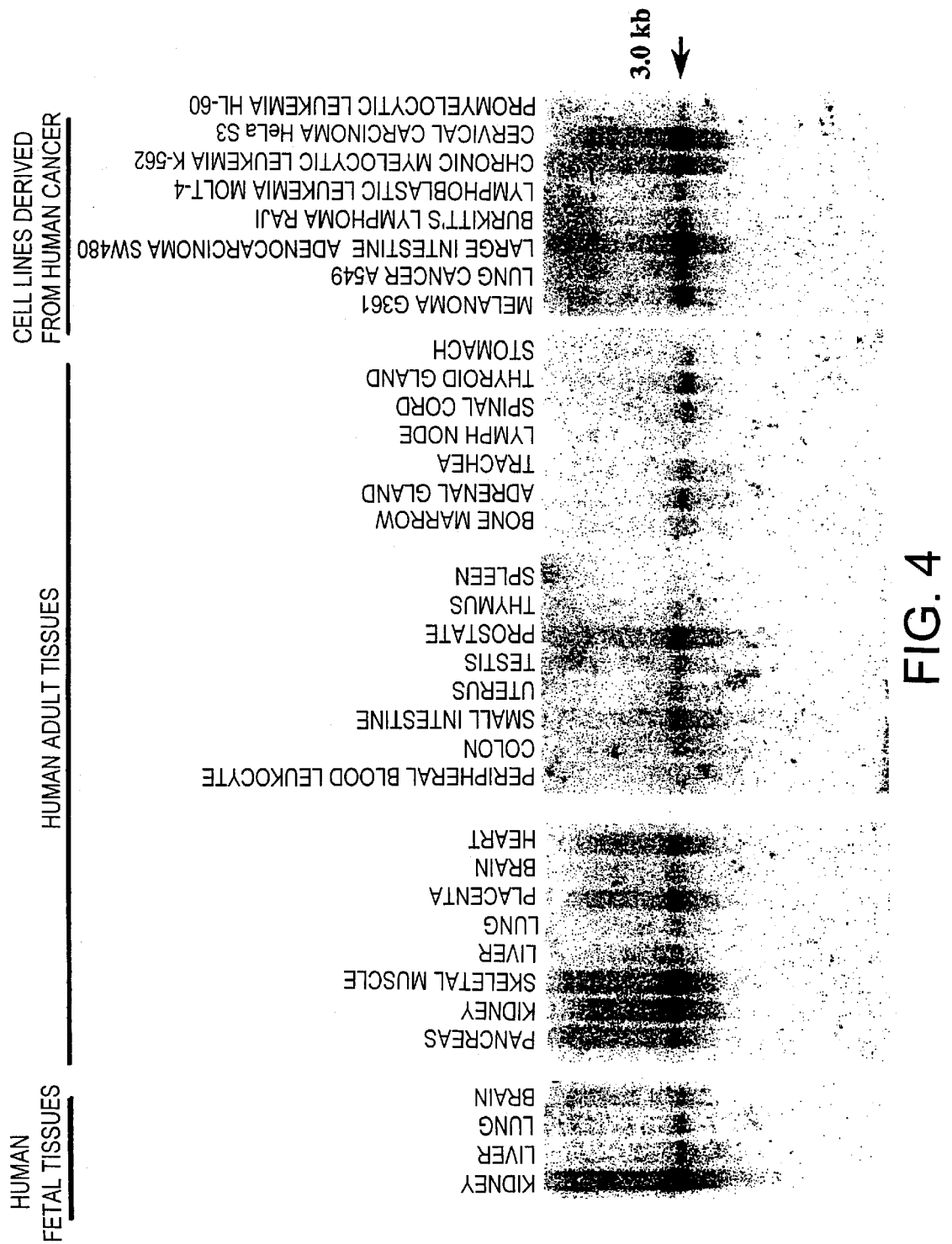
FIG. 4 represents electrophoretic patterns showing the results of Northern blot analysis of human OCTN2.

Northern analysis was performed using about 900 bp human OCTN2 cDNA as a probe which was obtained by PCR with a set of 631R S4 primer (5'-GTGCTGTTGGGCT CCTTCATTTCA-3', SEQ ID NO: 13) and 631R A1 primer (5'-AGCTGCATGAAGAGAAGGACACTG-3', SEQ ID NO: 14) in the same manner as for human OCTN1. The results are shown in FIG. 4. Although the expression pattern of human OCTN2 partly overlapped with that of human OCTN1, human OCTN2 differs from human OCTN1 in that the former was very intensely expressed in the kidney among fetal tissues, while the latter was strongly expressed also in cancer cell strains such as K-562, HeLa S3, SW480, etc. as well as the kidney, indicating that OCTN1 and OCTN2 may be involved in transport of substances such as carcinostatics in these cancer cells.

EXAMPLE 6

Forced Expression of Human OCTN1 in Human Fetal Kidney Cells (HEK293) and its Activity Determination Phage DNAs were extracted from positive phage clones obtained by screening the clones by the plaque hybridization method using the QIAGEN Lambda Kit (QIAGEN). After the DNA insert was subcloned into the pUC18 vector, cDNA containing the entire ORF which was cleaved out with SmaI and EcoRI was integrated between the EcoRI site and the blunted HindIII site of an expression vector for mammalian cells, pcDNA3 (Invitrogen), to obtain an expression plasmid DNA, pcDNA3/OCTN1. Plasmid DNA was prepared by alkaline-SDS method using the QIAGEN PLASMID MAXI Kit (QIAGEN).

The human fetal kidney-derived cell strain, HEK 293 cells were transfected with the plasmid pcDNA3/OCTN1 and PcDNA3 vector containing no insert as a control by the calcium phosphate method. First, the plasmid DNA (10 μg), a Hepes buffer solution (137 mM NaCl, 5 mM KCl, 0.7 mM $Na_2HPO_4$, 6 mM Dextrose, and 21 mM Hepes pH 7.1) (1 ml), and 2 M $CaCl_2$ (62.5 μl) were combined and allowed to stand at room temperature for 30 min or more to form calcium phosphate coprecipitates. After cells were plated on 10-cm plates at $1.5 \times 10^6$ cells per plate and cultured for 24 h, the calcium phosphate coprecipitates were added thereto, and the cells were further cultured for 24 h. Then, plates were washed with phosphate buffered saline (PBS), and the cells were further cultured for 24 h after the addition of fresh culture medium.

Transport experiment was performed using cells transfected with the plasmid DNA or untreated cells according to the following procedures. Cells were detached from plates using a rubber policeman, suspended in a is transport buffer (containing 125 mM NaCl, 4.8 mM KCl, 5.6 mM (+)-glucose, 1.2 mM $CaCl_2$, 1.2 mM $KH_2PO_4$, 1.2 mM $MgSO_4$, and 25 mM Hepes pH 7.4), and pre-incubated for 20 min. An appropriate amount of each labeled substrate ([$^{14}$C]TEA (tetraethylammonium) (NEN), [$^3$H]carnitine (L-carnitine hydrochloride) (Amersham), [$^3$H]PCG (benzylpenicillin) (Amersham), [$^3$H]quinidine (ARC), or [$^3$H]pyrilamine (mepyramine) (Amersham)) was then added to the cell suspension, and the resulting mixture was incubated at 37° C. for a predetermined period of time. Incubated cells were overlaid on a silicon layer prepared by layering a mixture of silicon oil and liquid paraffin (specific gravity=1.022) on a 3 M KCl layer, and separated by centrifugation. Radioactivity of cells was measured to determine the into-the-cell transport activity. In this case, $1 \times 10^6$ cells were used as one point of cells. HEK 293 cells were cultured in Dulbecco's MEM containing 10% fetal calf serum (FCS) in an atmosphere of 5% carbon dioxide at 37° C.

Figure 5:
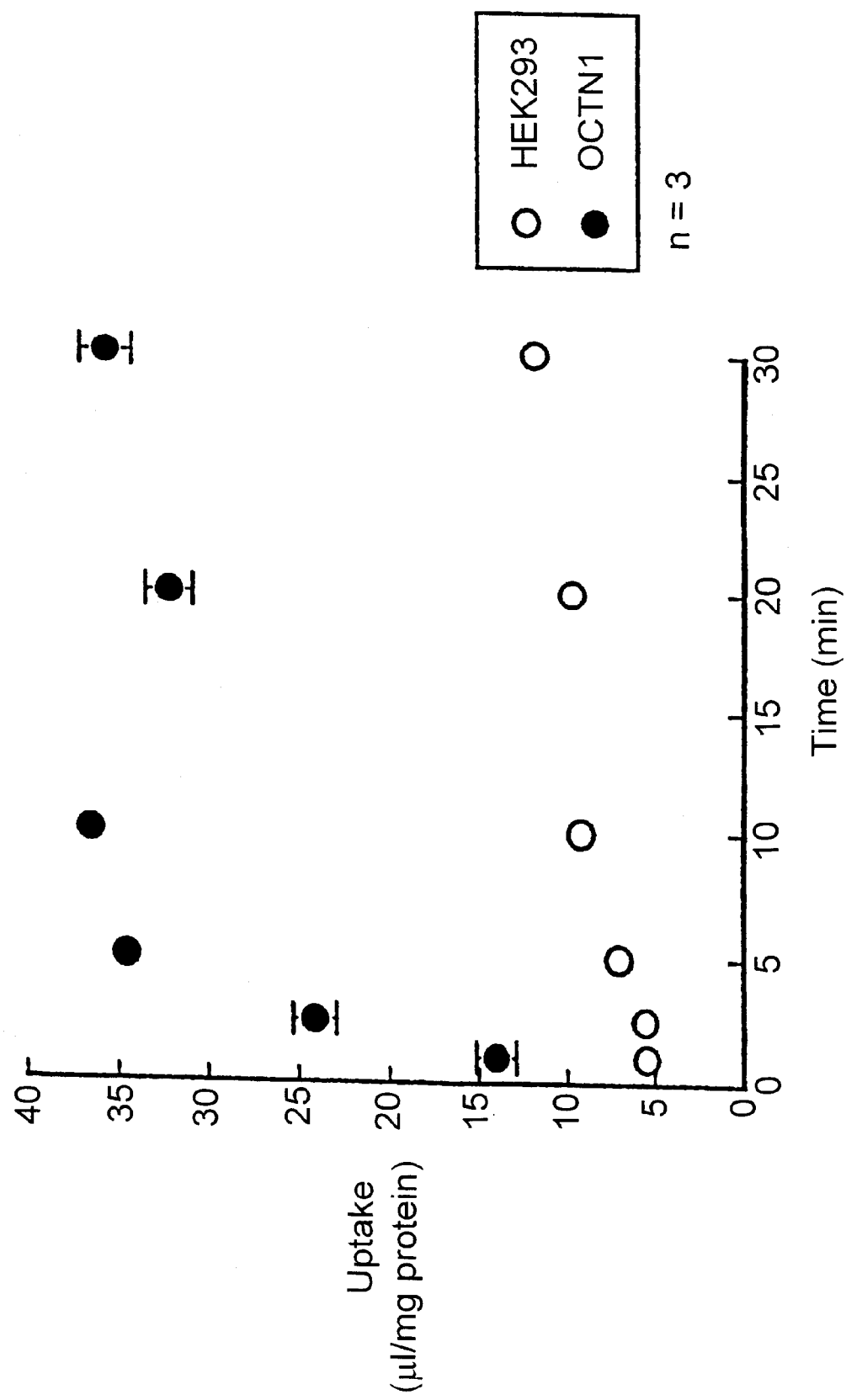
FIG. 5 is a graph showing the TEA-absorbing activity of human OCTN1. Clear circles represent untreated cells, and solid circles represent human OCTN1-transfected cells.
Figure 6:
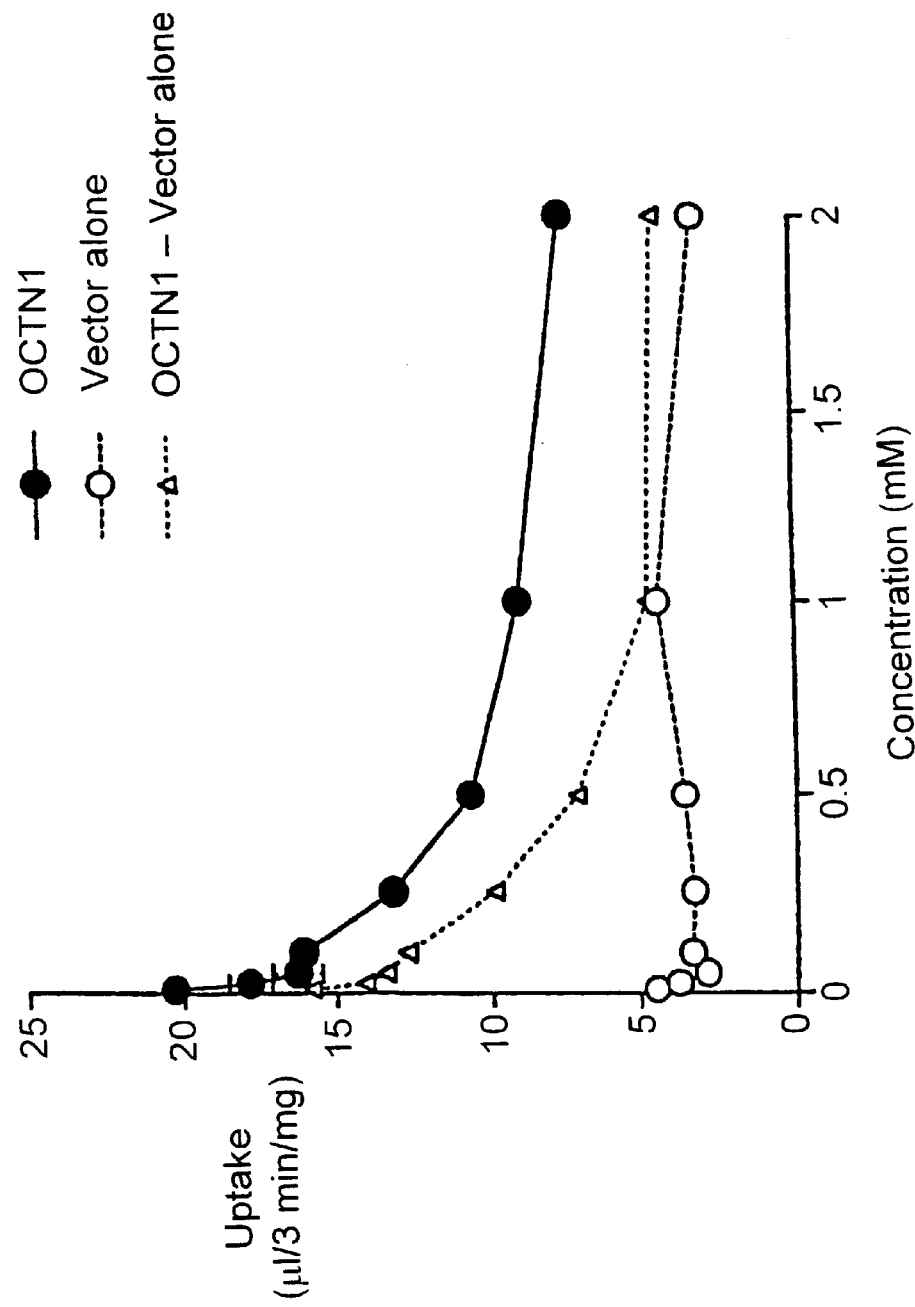
FIG. 6 is a graph showing effects of the cold TEA added in the experimental system in FIG. 5. In this graph, solid circles represent human OCTN1-transfected cells, and clear circles represent cells containing the vector with no insert. Clear triangles indicate the net uptake induced by human OCTN1 obtained by subtracting the clear circle values from the corresponding solid circle values.
Figure 7:
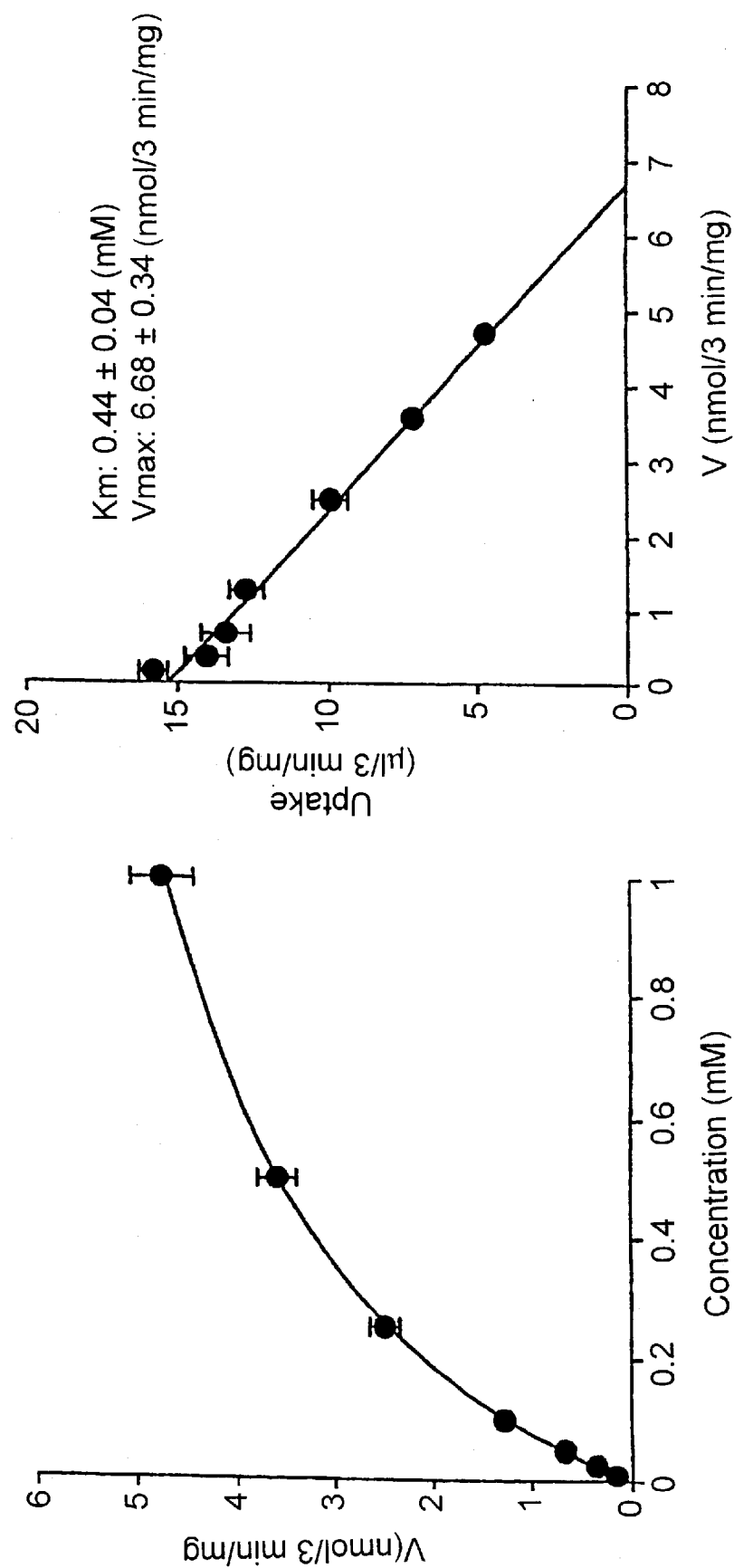
FIG. 7 is a graph showing TEA concentration-dependency of the TEA-absorbing activity of human OCTN1.
Figure 8:
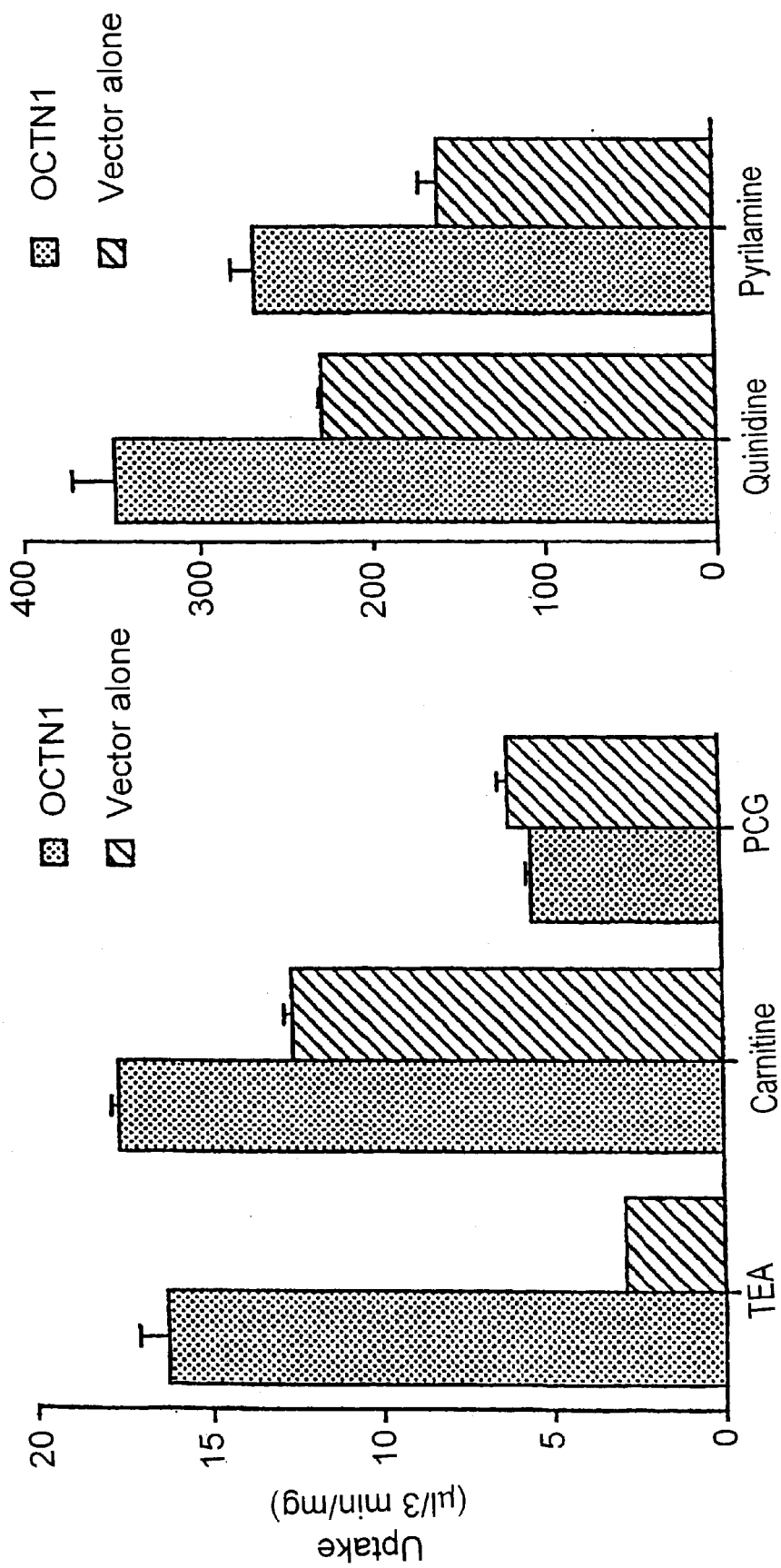
FIG. 8 is a bar graph showing the activity of the human OCTN1-transfected cells to absorb substances other than TEA.

First, the transporter capacity was measured in the cells transfected with pcDNA3/OCTN1 and untreated cells using TEA as a substrate (FIG. 5). A reaction time-dependent TEA uptake into the human OCTN1-transfectd cells was clearly observed. This uptake was not observed in untreated cells. Next, effects of the addition of unlabeled TEA on the labeled substrate uptake in this system (cold inhibition) was examined (FIG. 6). A decrease in the apparent uptake of the labeled substrate was clearly seen depending on the concentration of cold TEA added. In this experiment, almost no uptake of the substrate into cells was observed in cells transfected with the pcDNA3 vector containing no insert (Mock) used as a control like in untreated cells used, clearly indicating that this uptake phenomenon is due to the transfection of the cells with human OCTN1. Next, to obtain the Km (Michaelis constant) value of human OCTN1 to TEA, the uptake of $^{14}$C-TEA with various concentrations was measured (FIG. 7). From Lineweaver-Burk reciprocal plot of the net uptake obtained by subtracting the amount of the uptake in Mock cells from that in the human OCTN1-transfected cells, the Km value of 0.44±0.04 mM was obtained with the maximal velocity, Vmax of 6.68±0.34 (nmol/3 min/mg). Next, the transport capacity of human OCTN1 for other substrate than TEA was examined (FIG. 8). When the transport capacity was measured using labeled organic cations such as labeled carnitine, quinidine, and pyrilamine, a significant increase in the uptake of these compounds was clearly observed in human OCTN1-transfected cells as compared with Mock cells, clearly indicating that these organic cations can serve as substrates for human OCTN1. However, no significant increase in the uptake of an organic anion, PCG (benzylpenicillin), was observed.

EXAMPLE 7

Activity Measurement of Human OCTN1 Using Xenopus Oocytes cRNA was synthesized in vitro using T7 RNA polymerase with pcDNA3/OCTN1 as a template. This cRNA was diluted to the concentration of 0.3 ng/nl, and its 50-nl (15 ng) aliquot was injected into a single oocyte. As a control, 50 nl of distilled water was injected. These oocytes were cultured for 3 days, and then used for the transport experiment. After being preincubated in an uptake buffer (0.05% Tween 80, 100 mM NaCl, 2 mM KCl, 1 mM $CaCl_2$, 1 mM $MgCl_2$, and 10 mM Hepes pH 7.4) at 25° C. for 20 min, the oocytes were transferred to the uptake buffer containing 0.5 ml of labeled substrate to initiate the uptake. After the incubation at 25° C. for 1 h, the oocytes were washed in the ice-cold uptake buffer three times to terminate the reaction. The oocytes were solubilized in 5% SDS and mixed with Cleasol I (a cocktail for liquid scintillation counter) (3 ml) to determine the radioactivity. The radioactivity of the uptake buffer which contained the labeled compound at the time of incubation (external solution) (10 μl) was also similarly measured. The ratio of the radioactivity (dpm value) in the oocytes to that (dpm value) in the external solution was used as the uptake activity.

Figure 9:
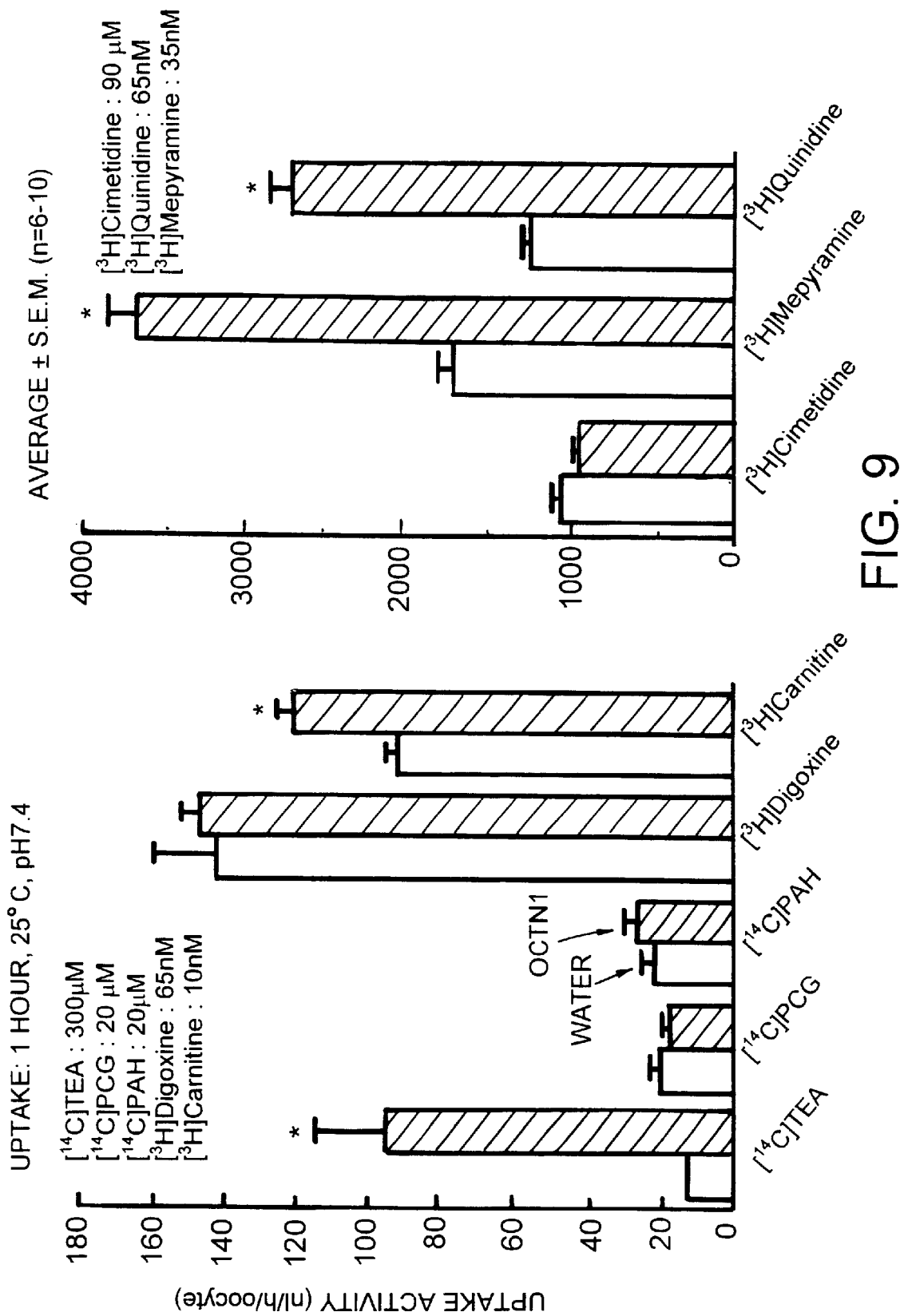
FIG. 9 is a bar graph showing the results of transport experiments using Xenopus oocytes. Bars indicated with "OCTN1" and "Water" represent the uptake activity of the human OCTN1-injected cRNA oocytes and that of the water-injected oocytes (containing no cRNA), respectively. Uptakes of TEA, carnitine, mepyramine, quinidine, and actinomycin D were observed in human OCTN1 cRNA-injected oocytes, whereas water-injected oocytes (containing no cRNA) exhibited almost no uptake activity.

Human OCTN1 also expresses the transport capacity for organic cations such as quinidine, mepyramine and carnitine, as well as TEA in this transport experiment system using Xenopus oocytes (FIG. 9).

Figure 10:
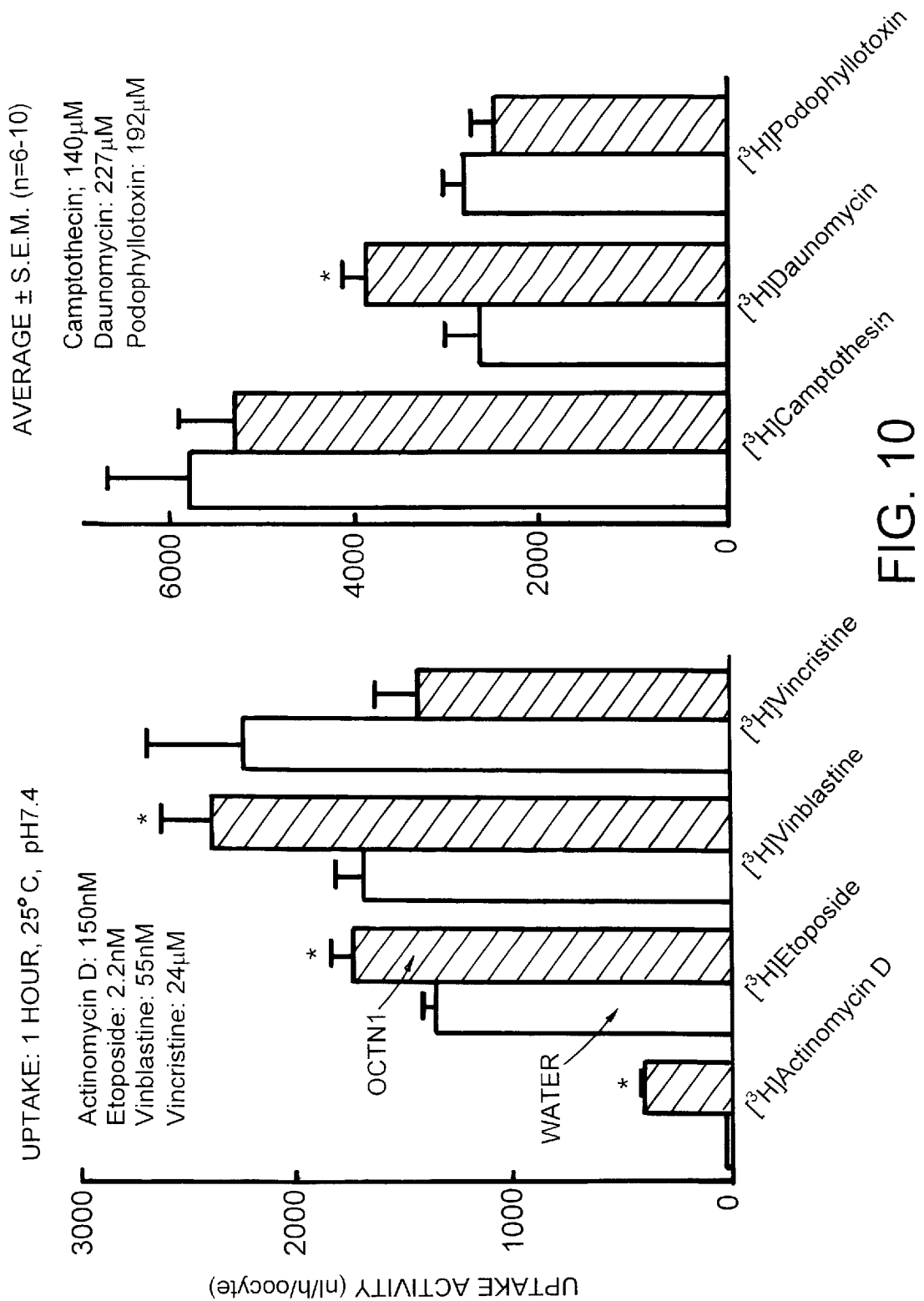
FIG. 10 is a bar graph showing the results of transport experiments for carcinostatics in Xenopus oocytes. Bars indicated with "OCTN1" and "Water" represent the uptake activity of the human OCTN1 cRNA-injected oocytes and that of the water-injected oocytes (containing no cRNA), respectively. Uptakes of actinomycin D, etoposide, vinblastine, and daunomycin were observed in the human OCTN1 cRNA-injected oocytes.

Next, the transport capacity of human OCTN1 for carcinostatics, etc. was examined. The results revealed that human OCTN1 has the activity to transport actinomycin D, etoposide, vinblastine, and daunomycin (FIG. 10). These results strongly indicate that OCTN1 would be involved in the into-the-cell translocation mechanism (mechanism for absorption for these drugs, which have been clinically used as carcinostatics. By designing and screening drugs utilizing the substrate specificity of OCTN1 so as to be readily recognized by this transporter, it would be possible to efficiently develop useful drugs that can be readily absorbed by the cells.

EXAMPLE 8

Forced Expression of Human OCTN2 in HEK Cells and its Activity Measurement

The expression plasmid DNA for human OCTN2 in mammalian cells was prepared as follows.

A single-stranded cDNA was synthesized from poly(A)$^+$ RNA derived from the human fetal kidney (CLONTECH) using the SuperScript™ II reverse transcriptase (GIBCO BRL). PCR was performed using the thus-obtained cDNA as a template under the following conditions to amplify 5'- and 3'-end fragments of human OCTN2.

For the amplification of 5'-end fragment (about 800 bp) of human OCTN2, OCTN2 3 primer (5'-GATGGATCCCGGA CGGTCTTGGGTCGCCTGCTG-3', SEQ ID NO: 16) and OCN2 4 primer (5'-GATGGATCCAAATGCTGCCACATA GTTGGAGAT-3', SEQ ID NO: 17) were used. PCR was carried out using DNA polymerase ExTaq (TaKaRa) and dNTPs (150 μM 7-deaza dGTP, 50 μM dGTP, 200 μM dATP, 200 μM dTTP, and 200 μM dCTP) according to the following conditions: 94° C. for 2 min; 35 cycles of 94° C. for 30 s, 63° C. for 1 min, and 72° C. for 2 min,; and 72° C. for 10 min. For the amplification of 3'-end fragment (about 1.2 kbp) of human OCTN2, OCTN2 7 primer (5'-GATGGATCCATGGGCATGCAGACAGGCTTCAGC-3', SEQ ID NO: 18) and OCTN2 8 primer (5'-GATGGATC CTTCCTCTTCAGTTTCTCCCTTACT-3', SEQ ID NO: 19) were used. PCR was carried out using DNA polymerase ExTaq (TaKaRa) and dNTPs (200 μM dGTP, 200 μM DATP, 200 μM dTTP, and 200 μM dCTP) according to the following conditions: 94° C. for 2 min; 35 cycles of 94° C. for 30 s, 63° C. for 30 s, and 72° C. for 2 min,; and 72° C. for 10 min.

These fragments were respectively electrophoresed on agarose gel, excised from the gel, purified, and subcloned into the pT7Blue-T vector. Clones having no PCR error were selected by sequencing, and clones from both fragments were ligated at the PstI site in the overlapping region. Each ligated fragment was eventually incorporated into the BamHI site of the pcDNA3 vector, and used as the expression plasmid DNA pcDNA3/OCTN2.

Figure 11:
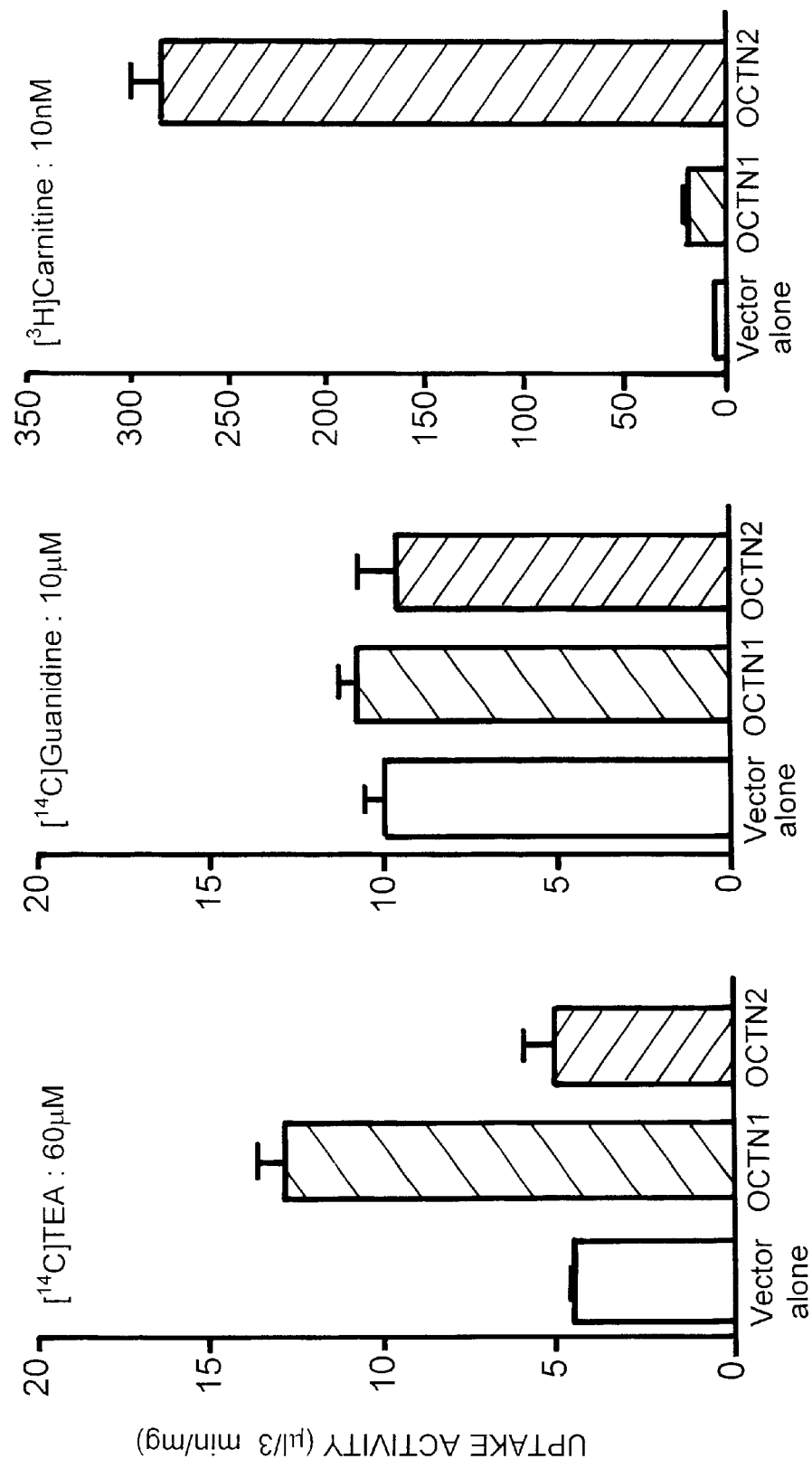
FIG. 11 is a bar graph showing the results of transport experiments with human OCTN1 and human OCTN2 in HEK293 cells. Human OCTN1 has the efficient transport activity for TEA and human OCTN2 for carnitine.

HEK cells were transfected with pcDNA3/OCTN2, the pcDNA3 vector containing no insert (Mock), or pcDNA3/OCTN1 by the method described in Example 6 to perform transport experiments. It was proved that human OCTN2 has a high capacity to efficiently transport carnitine (FIG. 11). On the other hand, human OCTN2 hardly transported TEA, which were efficiently transported by human OCTN1, revealing that they clearly differ in their substrate specificities.

Figure 12:
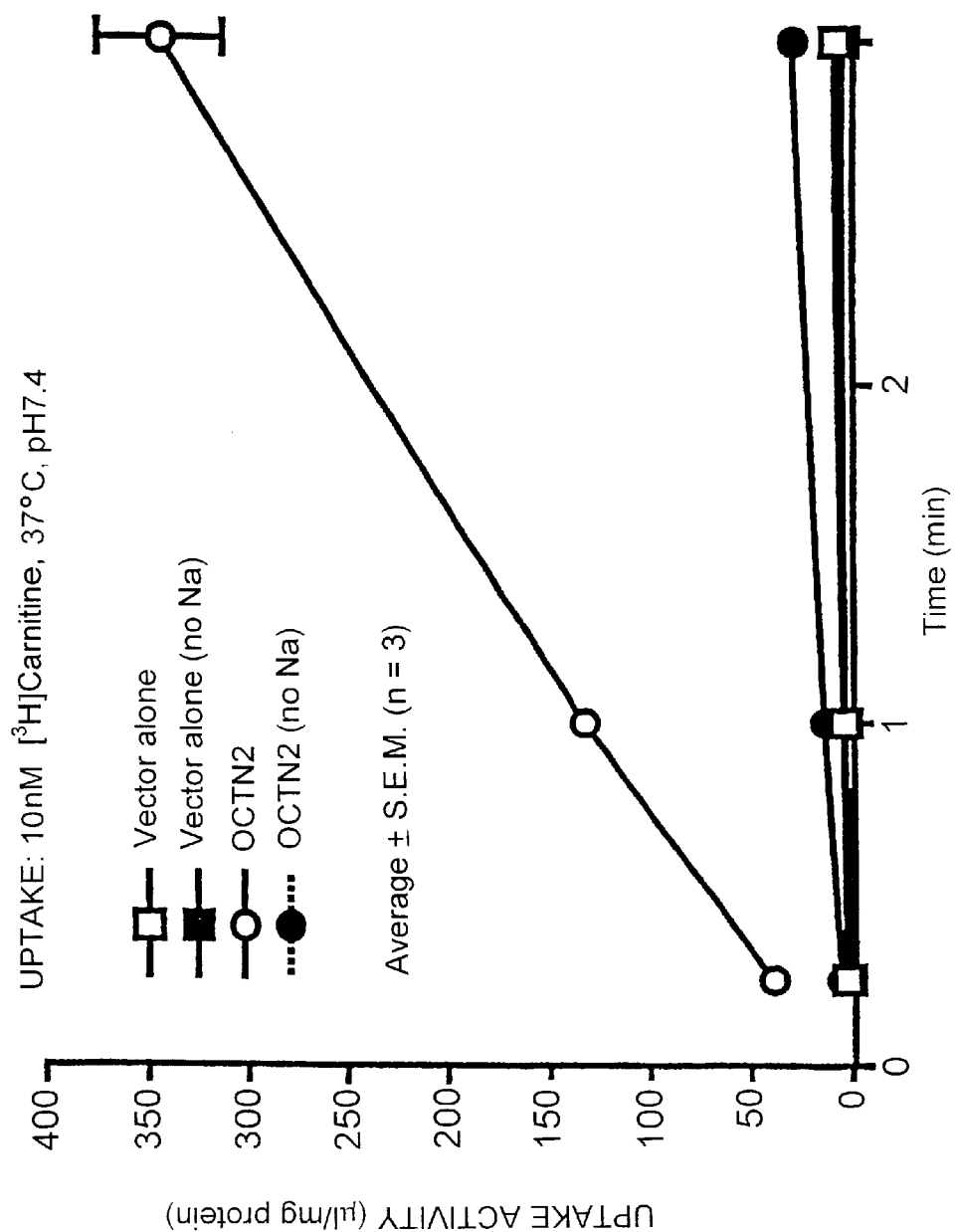
FIG. 12 is a graph showing the results of $Na^+$-dependency of the carnitine transport activity of human OCTN2. Human OCTN2 exhibits a time-dependent carnitine transport activity (clear circle) in the presence of $Na^+$, while no such activity in the absence of $Na^+$ (solid circle), indicating that the carnitine transport activity of human OCTN2 depends on the presence of $Na^+$.

Next, Na$^+$ dependence of human OCTN2-mediated carnitine transport was examined using a transport buffer in which Na$^+$ was replaced with K$^+$ (FIG. 12). The result showed that carnitine transport mediated by human OCTN2 completely depended on the presence of Na$^+$, indicating that OCTN2 is a symport type transporter that transports substrates and Na$^+$ in the same direction.

EXAMPLE 9

Cloning of Mouse OCTN1

Data base search using human OCTN1 cDNA sequence detected several Expressed Sequence Tags (ESTS) derived from mouse, which had very high homology to the human OCTN1 cDNA sequence. Based on these EST sequences, MONL 1 primer (5'-CGCGCCGAATCGCTGAATC CTTTC-3', SEQ ID NO: 20) and MONA 4 primer (5'-AGGCTTTTGATTTGTTCTGTTGAG-3', SEQ ID NO: 21) were prepared. PCR was performed using a set of these primers and cDNA prepared from poly(A)$^+$ RNA derived from the mouse kidney as a template. As a result, fragments of about 2 kbp were amplified. These fragments were electrophoresed on agarose gels, excised from the gels, purified, and subcloned into the pT7Blue T vector (Novagen) by the TA cloning method. The sequence of mouse OCTN1 was determined by sequencing plural clones. The nucleotide sequence of cDNA thus determined is shown in SEQ ID NO: 23, and amino acid sequence of the protein encoded by the cDNA in SEQ ID NO: 22.

EXAMPLE 10

Cloning of Mouse OCTN2

First, MONB 20 primer (5'-CCCATGCCAACAAGGAC AAAAAGC-3', SEQ ID NO: 24) was prepared from the sequence of human OCTN2 cDNA. The Marathon-Ready™ cDNA derived from the mouse kidney (CLONTECH) was used as a template for the 5'-Rapid Amplification of cDNA ends (RACE) to clone the 5'-end sequence upstream of the primer. Next, data base search was performed using human OCTN2 nucleotide sequence to detect several ESTs derived from mouse, which had a very high homology with human OCTN2. MONB 26 primer (5'-ACAGAACAGAA AAGCCCTCAGTCA-3', SEQ ID NO: 25) was prepared from these EST sequences. MONB 6 primer (5'-TGTTTT TCGTGGGTGTGCTGATGG-3', SEQ ID NO: 26) was prepared from the sequence obtained by the 5'-RACE. PCR was performed using this primer and MONB 26 primer and cDNA prepared from poly(A)$^+$ RNA derived from the mouse kidney as a template to amplify the 3'-end fragments. The sequence of mouse OCTN2 was determined by sequencing directly of after subcloning respective fragments. The nucleotide sequence of the cDNA thus determined is shown in SEQ ID NO: 28, and amino acid sequence of the protein encoded by the cDNA in SEQ ID NO: 27.

EXAMPLE 11

Tissue Expression Analysis of Mouse OCTN1 and Mouse OCTN2

Figure 13:
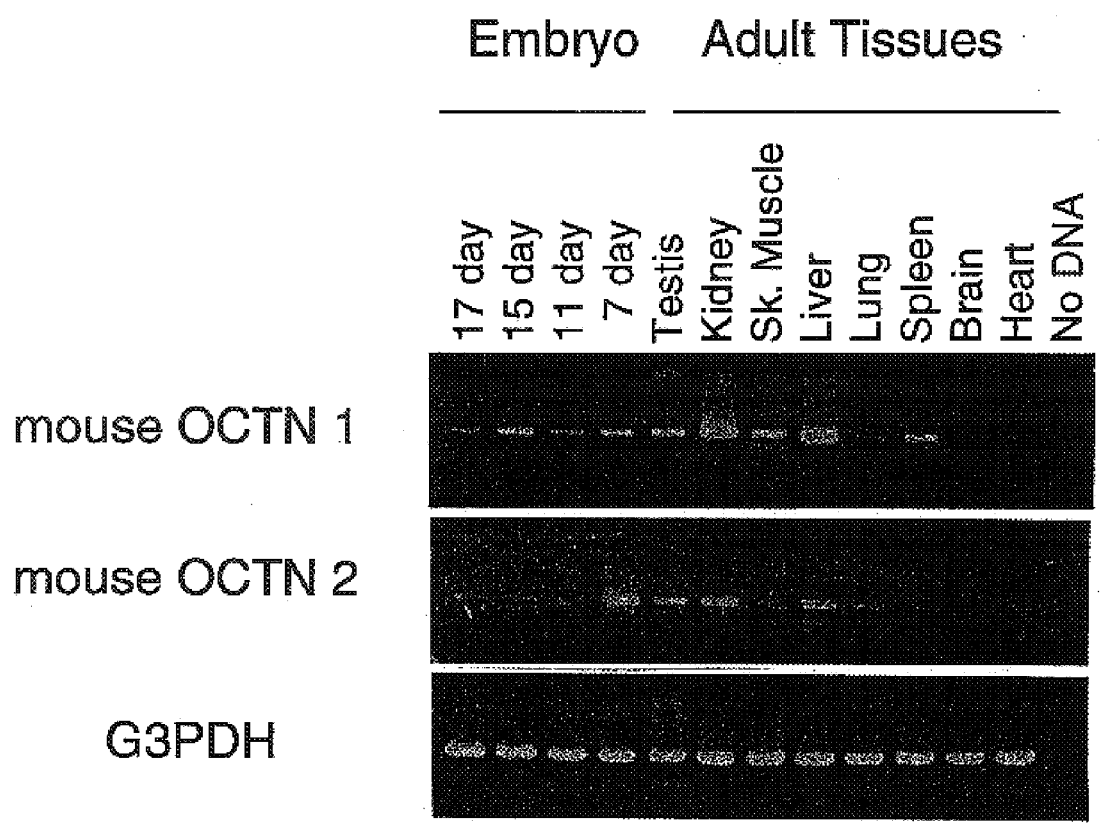
FIG. 13 shows the expression of mouse OCTN1 and mouse OCTN2 genes detected by RT-PCR amplification in each tissue. G3PDH serves as a control, indicating that the amount of cDNA in each tissue is uniform.

The expression amount of mouse OCTN1 and mouse OCTN2 genes in various tissues was examined by RT-PCR using a mouse Multiple Tissue cDNA (MTC) panel (CLONTECH) (FIG. 13). Primers used are MONL 1 and MONA 4 for mouse OCTN1, and MONB 6 and MONB 26 for mouse OCTN2. As a result, the high level expression of mouse OCTN1 was detected in the kidney and liver, while that of mouse OCTN2 in the kidney, liver, and 7-days old embryo.

Industrial Applicability

This invention provides a family of novel organic cation transporter genes and proteins encoded by these genes.

Transporter proteins of this invention are useful for developing newly designed drugs that can be transported mediated by these proteins, and pharmaceuticals for disorders caused by functional abnormalities of the proteins.

What is claimed is:

1. A substantially pure polypeptide comprising an amino acid sequence at least 76% identical to SEQ ID NO:1, wherein the polypeptide is a transporter of an organic cation.

2. The polypeptide of claim 1, wherein the amino acid sequence is at least 80% identical to SEQ ID NO:1.

3. The polypeptide of claim 1, wherein the amino acid sequence is at least 90% identical to SEQ ID NO:1.

4. The polypeptide of claim 1, wherein the amino acid sequence is at least 95% identical to SEQ ID NO:1.

5. A substantially pure polypeptide comprising the sequence of SEQ ID NO:1.

6. A substantially pure polypeptide comprising the amino acid sequence of SEQ ID NO:1, with up to 30 conservative amino acid substitutions, wherein the polypeptide is a transporter of an organic cation.

7. A substantially pure polypeptide encoded by a nucleic acid that hybridizes to a probe the sequence of which consists of SEQ ID NO:2, under conditions of: hybridization at 68°, followed by washing in 2×SSC/0.1% SDS for 20 minutes at room temperature and twice in 0.1×SSC/0.1% SDS for 20 minutes at 50°,
wherein the polypeptide is a transporter of an organic cation.

8. A substantially pure polypeptide consisting of the sequence of SEQ ID NO:1.

9. A substantially pure polypeptide comprising an amino acid sequence at least 76% identical to SEQ ID NO: 1, wherein the polypeptide is a transporter of an organic cation, and wherein the polypeptide comprises the sequence: Xaa1-Xaa2-Xaa3-Xaa4-Xaa5-Xaa6-Xaa7-Gly-Arg-Xaa8-Xaa9-Xaa10-Xaa11-Xaa12, wherein Xaa1 is Leu, Ile, Val, Met, Ser, Thr, Ala, or Gly;
Xaa2 is Leu, Ile, Val, Met, Phe, Ser, Ala, or Gly;
Xaa3 is any amino acid;
Xaa4 is Leu, Ile, Val, Met, Ser, Ala;
Xaa5 is Asp or Glu;
Xaa6 is any amino acid;
Xaa7 is Leu, Ile, Val, Met, Phe, Tyr, Trp, or Ala;
Xaa8 is Arg or Lys;
Xaa9 is any amino acid;
Xaa10 is any amino acid;
Xaa11 is any amino acid; and
Xaa12 is Gly, Ser, Thr, or Ala.

10. The polypeptide of claim 9, wherein the amino acid sequence at least 80% identical to SEQ ID NO:1.

11. The polypeptide of claim 9, wherein the amino acid sequence at least 90% identical to SEQ ID NO:1.

12. The polypeptide of claim 9, wherein the amino acid sequence at least 95% identical to SEQ ID NO:1.

13. A substantially pure polypeptide comprising an amino acid sequence at least 76% identical to SEQ ID NO:1, wherein the polypeptide is a transporter of an organic cation, and wherein the polypeptide has 11 to 12 transmembrane domains.

14. The polypeptide of claim 13, wherein the amino acid sequence at least 80% identical to SEQ ID NO:1.

15. The polypeptide of claim 13, wherein the amino acid sequence at least 90% identical to SEQ ID NO:1.

16. The polypeptide of claim 13, wherein the amino acid sequence at least 95% identical to SEQ ID NO:1.

17. A substantially pure polypeptide comprising an amino acid sequence at least 76% identical to SEQ ID NO: 1, wherein the polypeptide is a transporter of an organic cation, and wherein the polypeptide has a GTP/ATP binding domain ([Ala, Gly]-Xaa(4)-Gly-Lys-[Ser, Thr].

18. The polypeptide of claim 17, wherein the amino acid sequence at least 80% identical to SEQ ID NO:1.

19. The polypeptide of claim 17, wherein the amino acid sequence at least 90% identical to SEQ ID NO:1.

20. The polypeptide of claim 17, wherein the amino acid sequence at least 95% identical to SEQ ID NO:1.

21. A substantially pure polypeptide comprising an amino acid sequence at least 76% identical to SEQ ID NO:1, wherein the polypeptide is a transporter of an organic cation, and wherein the polypeptide has (a) 11 to 12 transmembrane domains, (b) a GTP/ATP binding domain ([Ala, Gly]-Xaa(4)-Gly-Lys-[Ser, Thr], and (c) the sequence: Xaa1-Xaa2-Xaa3-Xaa4-Xaa5-Xaa6-Xaa7-Gly-Arg-Xaa8-Xaa9-Xaa10-Xaa11-Xaa12, wherein Xaa is any amino acid;

Xaa1 is Leu, Ile, Val, Met, Ser, Thr, Ala, or Gly;

Xaa2 is Leu, Ile, Val, Met, Phe, Ser, Ala, or Gly;

Xaa3 is any amino acid;

Xaa4 is Leu, Ile, Val, Met, Ser, Ala;

Xaa5 is Asp or Glu;

Xaa6 is any amino acid;

Xaa7 is Leu, Ile, Val, Met, Phe, Tyr, Trp, or Ala;

Xaa8 is Arg or Lys;

Xaa9 is any amino acid;

Xaa10 is any amino acid;

Xaa11 is any amino acid; and

Xaa12 is Gly, Ser, Thr, or Ala.

22. The polypeptide of claim 21, wherein the amino acid sequence at least 80% identical to SEQ ID NO:1.

23. The polypeptide of claim 21, wherein the amino acid sequence at least 90% identical to SEQ ID NO:1.

24. The polypeptide of claim 21, wherein the amino acid sequence at least 95% identical to SEQ ID NO:1.

25. A substantially pure human transport polypeptide comprising an amino acid sequence at least 76% identical to SEQ ID NO:1, wherein the polypeptide is a transporter of an organic cation, and wherein the polypeptide has (a) 11 to 12 transmembrane domains, (b) a GTP/ATP binding domain ([Ala, Gly]-Xaa(4)-Gly-Lys-[Ser, Thr], and (c) the sequence: Xaa1-Xaa2-Xaa3-Xaa4-Xaa5-Xaa6-Xaa7-Gly-Arg-Xaa8-Xaa9-Xaa10-Xaa11-Xaa12, wherein Xaa is any amino acid;

Xaa1 is Leu, Ile, Val, Met, Ser, Thr, Ala, or Gly;

Xaa2 is Leu, Ile, Val, Met, Phe, Ser, Ala, or Gly;

Xaa3 is any amino acid;

Xaa4 is Leu, Ile, Val, Met, Ser, or Ala;

Xaa5 is Asp or Glu;

Xaa6 is any amino acid;

Xaa7 is Leu, Ile, Val, Met, Phe, Tyr, Trp, or Ala;

Xaa8 is Arg or Lys;

Xaa9 is any amino acid;

Xaa10 is any amino acid;

Xaa11 is any amino acid; and

Xaa12 is Gly, Ser, Thr, or Ala.

26. The polypeptide of claim 25, wherein the amino acid sequence at least 80% identical to SEQ ID NO:1.

27. The polypeptide of claim 25, wherein the amino acid sequence at least 90% identical to SEQ ID NO:1.

28. The polypeptide of claim 25, wherein the amino acid sequence at least 95% identical to SEQ ID NO:1.

* * * * *

UNITED STATES PATENT AND TRADEMARK OFFICE
Certificate

Patent No. 6,759,514 B1                                                                        Patented: July 6, 2004

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Jun-ichi Nezu, Gotemba (JP); Asuka Oku, Shiroi (JP); and Akira Tsuji, Kanazawa (JP).

Signed and Sealed this Nineteenth Day of February 2013.

*VANESSA L. FORD*
*Supervisory Patent Examiner*
*Art Unit 1646*
*Technology Center 1600*